(12) United States Patent
Hoefle et al.

(10) Patent No.: US 7,235,669 B2
(45) Date of Patent: Jun. 26, 2007

(54) EPOTHILONE SIDE COMPONENTS

(75) Inventors: Gerhard Hoefle, Braunschweig (DE); Hans Reichenbach, Braunschweig (DE); Klaus Gerth, Braunschweig (DE); Ingo Hardt, Braunschweig (DE); Florenz Sasse, Braunschweig (DE); Heinrich Steinmetz, Braunschweig (DE)

(73) Assignee: Helmholtz-Zentrum fur Infektionsforschung, GmbH, Braunschweig (DE)

( * ) Notice: Subject to any disclaimer, the term of this patent is extended or adjusted under 35 U.S.C. 154(b) by 0 days.

(21) Appl. No.: 11/354,769

(22) Filed: Feb. 15, 2006

(65) Prior Publication Data

US 2006/0142584 A1 Jun. 29, 2006

Related U.S. Application Data

(60) Continuation of application No. 10/457,098, filed on Jun. 6, 2003, now abandoned, which is a division of application No. 09/719,932, filed as application No. PCT/EP99/04244 on Jun. 18, 1999, now Pat. No. 6,624,310.

(30) Foreign Application Priority Data

Jun. 18, 1998 (DE) ............................... 198 26 988

(51) Int. Cl.
*C07D 417/06* (2006.01)
(52) U.S. Cl. ..................................... 548/203
(58) Field of Classification Search ............... 548/204, 548/203
See application file for complete search history.

(56) References Cited

U.S. PATENT DOCUMENTS

| | | | |
|---|---|---|---|
| 5,969,145 A | 10/1999 | Schinzer et al. | |
| 6,204,388 B1 | 3/2001 | Danishefsky et al. | |
| 6,284,781 B1 * | 9/2001 | Danishefsky et al. | 514/365 |
| 6,288,237 B1 | 9/2001 | Hoefle et al. | |
| 6,303,342 B1 | 10/2001 | Julien et al. | |
| 6,359,140 B1 | 3/2002 | Höfle et al. | |
| 6,365,749 B1 | 4/2002 | Kim et al. | |
| 6,380,394 B1 | 4/2002 | Nicolaou et al. | |
| 6,380,395 B1 | 4/2002 | Vite et al. | |
| 6,441,186 B1 | 8/2002 | Nicolaou et al. | |
| 6,605,599 B1 | 8/2003 | Vite et al. | |
| 6,613,912 B2 | 9/2003 | Hoefle et al. | |
| 6,831,076 B2 | 12/2004 | Hoefle et al. | |

FOREIGN PATENT DOCUMENTS

| | | |
|---|---|---|
| WO | WO 97/19086 | 5/1997 |
| WO | WO 98/08849 | 3/1998 |
| WO | WO 98/22461 | 5/1998 |
| WO | WO 98/25929 | 6/1998 |
| WO | WO 99/01124 | 1/1999 |
| WO | WO 99/02514 | 1/1999 |
| WO | WO 99/07692 | 2/1999 |
| WO | WO 99/27890 | 6/1999 |
| WO | WO 99/43653 | 9/1999 |
| WO | WO 99/54319 | 10/1999 |
| WO | WO 99/65913 | 12/1999 |
| WO | WO 00/00485 | 1/2000 |
| WO | WO 00/31247 | 6/2000 |
| WO | WO 00/49012 | 8/2000 |
| WO | WO 98/25929 | 11/2002 |

OTHER PUBLICATIONS

Nicolaou et al. Synthesis of epothilones A and B in solid and solution phase. 1997, Nature vol. 387, pp. 268-272.
Nicolaou et al., 1998, "Chemical Biology of Epothilones", Angew. Chem. Int. Ed. Engl. 37:2014-2045.
Bollag et al., "Epothilones, a New Class of Microtubule-stabilizing Agents with Taxol-like Mechanism of Action", Cancer Research 55, pp. 2325-2333 (1995).

* cited by examiner

*Primary Examiner*—Long V. Le
*Assistant Examiner*—Shafiqul Haq
(74) *Attorney, Agent, or Firm*—Gary D. Greenblatt; Anastasia P. Winslow

(57) ABSTRACT

The invention concerns compounds which can be obtained by fermenting DSM 6773, especially epothilones A1, A2, A8, A9, B10, C1, C2, C3, C4, C5, C6, C7, C8, C9, D1, D2, D5, G1, G2, H1, H2, I1, I2, I3, I4, I5, I6 and K and trans-epothilones C1 and C2.

12 Claims, 2 Drawing Sheets

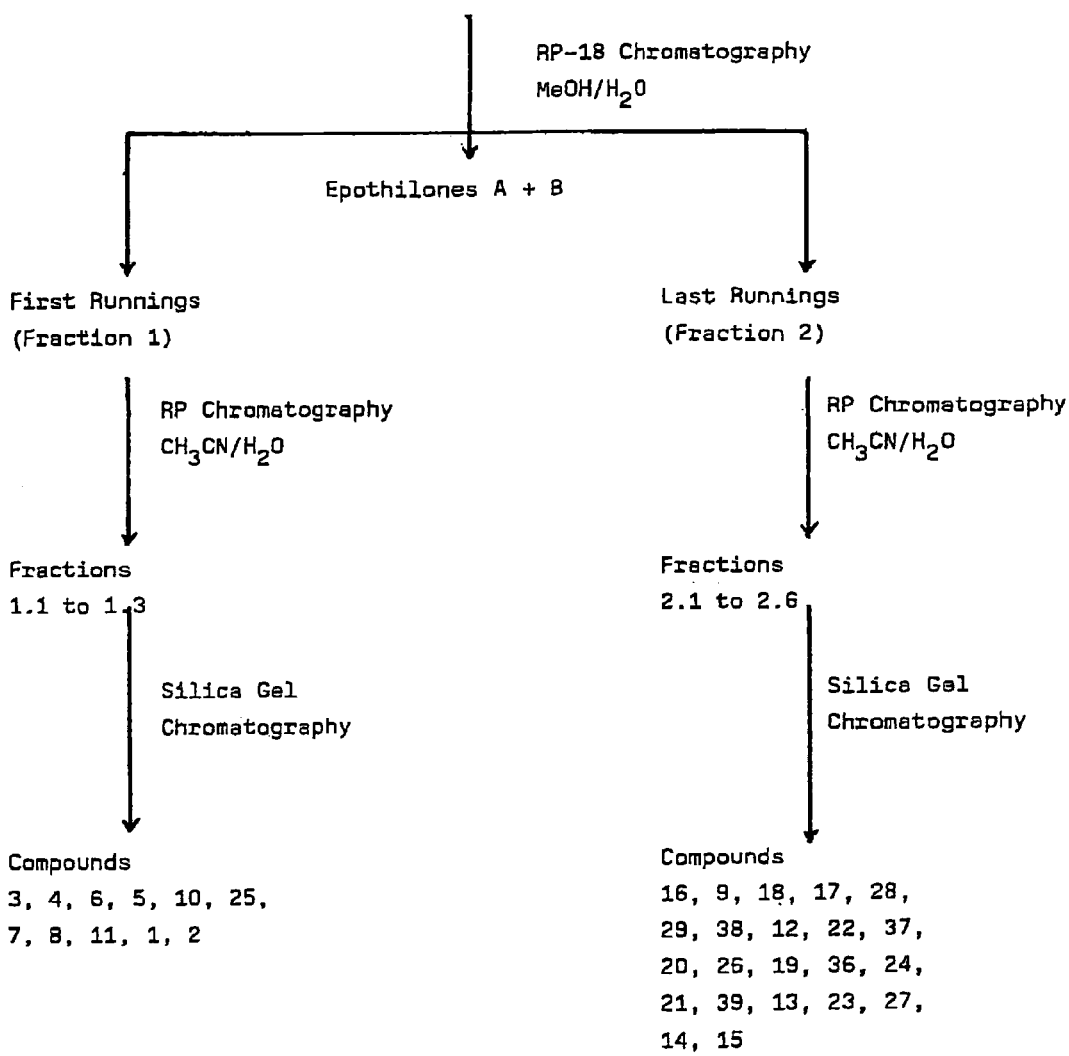

Fig. 2

| | | | |
|---|---|---|---|
| | | Epothilone E (3) | variable[a] |
| | | Epothilone F (4) | variable[a] |
| fraction 1 | 1.1 | Epothilone A₂ (6) | 14.5 mg |
| | | Epothilone A₁ (5) | 3.1 mg |
| | | Epothilone G₁ (10) | 62.3 mg |
| | | Epothilone C₇ (25) | 0.9 mg |
| | 1.2 | Epothilone A₃ (7) | 38.7 mg |
| | | Epothilone A₀ (8) | 4.4 mg |
| | 1.3 | Epothilone G₂ (11) | 9.4 mg |
| | | Epothilone A (1) | 29800.0 mg |
| | | Epothilone B (2) | 10300.0 mg |
| fraction 2 | 2.1 | Epothilone C₁ (16) | 32.4 mg |
| | | Epothilone B₁₀ (9) | 1.1 mg |
| | 2.2 | Epothilone C₂ (18) | 58.4 mg |
| | 2.3 | Epothilone D₁ (17) | 5.3 mg |
| | | trans-Epothilone C₁ (28) | 1.4 mg |
| | | trans-Epothilone C₂ (29) | 4.5 mg |
| | | 38 | 6.6 mg |
| | | Epothilone H₁ (12) | 3.0 mg |
| | | Epothilone C₅ (22) | 7.3 mg |
| | 2.4 | 37 | 2.9 mg |
| | | Epothilone C₃ (20) | 32.5 mg |
| | | Epothilone C₄ (26) | 26.3 mg |
| | 2.5 | Epothilone D₂ (19) | 13.1 mg |
| | | Epothilone K (36) | 0.4 mg |
| | | Epothilone C₆ (24) | 2.8 mg |
| | | Epothilone C₄ (21) | 6.5 mg |
| | 2.6 | 39 | 0.8 mg |
| | | Epothilone H₂ (13) | 1.5 mg |
| | | Epothilone D₆ (23) | 0.9 mg |
| | | Epothilone C₉ (27) | 3.0 mg |
| | | Epothilone C (14) | 4600.0 mg |
| | | Epothilone D (15) | 2700.0 mg |

EPOTHILONE SIDE COMPONENTS

This application is a continuation application of U.S. patent application Ser. No. 10/457,098, filed Jun. 6, 2003 now abandoned, which is a divisional application of Ser. No. 09/719,932 now U.S. Pat. No. 6,624,310, filed Mar. 21, 2001, which is the U.S. National Stage of PCT/EP99/04244, filed Jun. 18, 1999, which claims priority to DE 19826988.9, filed Jun. 18, 1998, the disclosures of each are herein incorporated by reference in their entireties.

The invention concerns compounds which in the present context are designated epothilone side components, viz. compounds 5 to 13 and 16 to 39. These compounds can be produced by fermenting DSM 6773 in accordance to DE 41 38 042.8.

Characterizing data of the compounds according to the invention will be compiled as follows.

Production: The processing of a raw epothilone mixture, which has been produced by fermenting DSM 6773 in a 900 l fermentor, can be drawn schematically from FIGS. 1 to 2.

Activities: cf. table 1.

BRIEF DESCRIPTION OF THE FIGURES

FIG. 1 is a separation scheme for the raw epothilones into fractions and the fractions into compounds.

FIG. 2 is a schematic diagram showing the separation of the fractions into separate compounds and the amounts of said compounds.

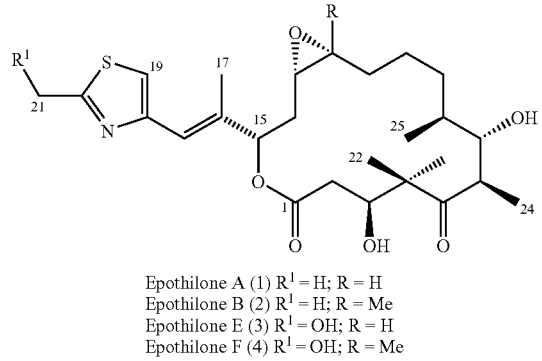

Epothilone A (1) $R^1$ = H; R = H
Epothilone B (2) $R^1$ = H; R = Me
Epothilone E (3) $R^1$ = OH; R = H
Epothilone F (4) $R^1$ = OH; R = Me

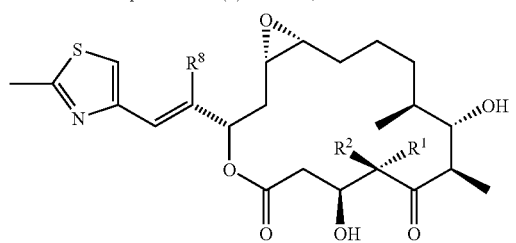

Epothilone $A_1$ (5) $R^1$ = H; $R^2$, $R^8$ = Me
Epothilone $A_2$ (6) $R^2$ = H; $R^1$, $R^8$ = Me
Epothilone $A_8$ (7) $R^8$ = H; $R^1$, $R^2$ = Me
Epothilone $A_9$ (8) $R^1$ = CH$_2$OH; $R^2$, $R^8$ = Me

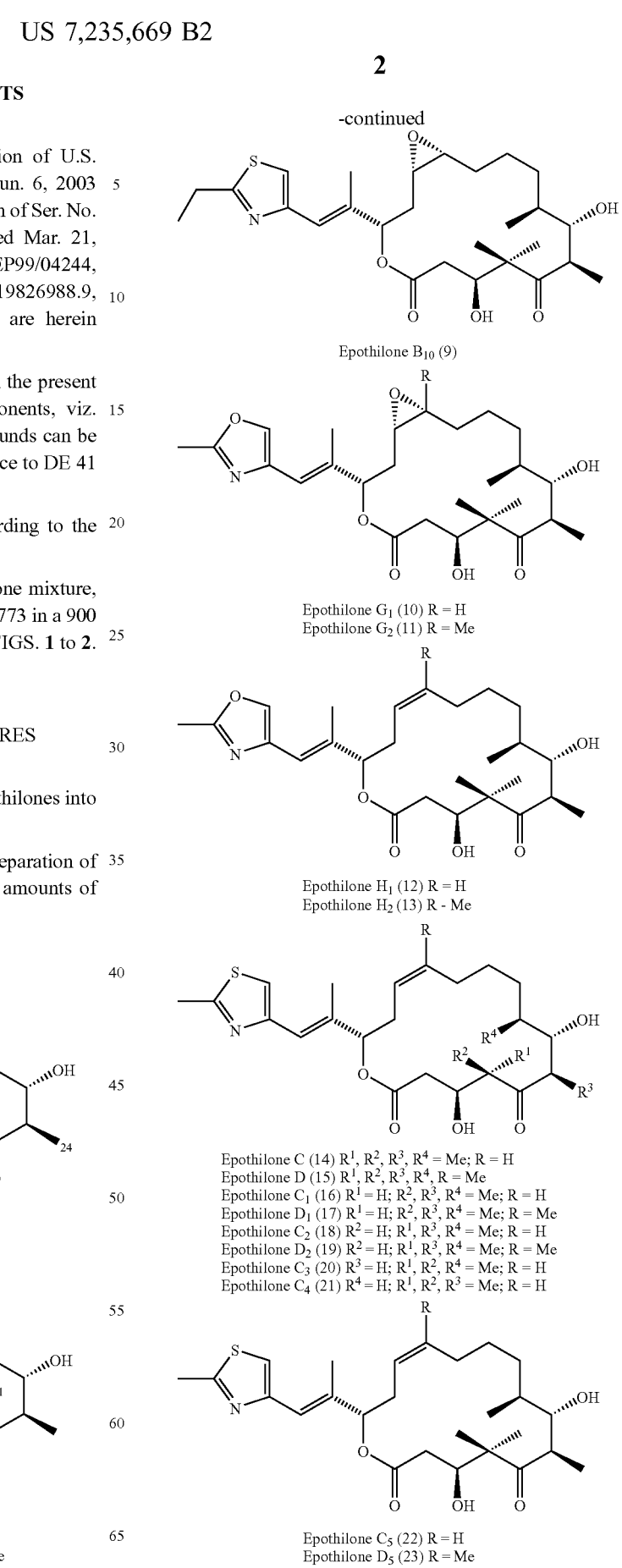

Epothilone $B_{10}$ (9)

Epothilone $G_1$ (10) R = H
Epothilone $G_2$ (11) R = Me

Epothilone $H_1$ (12) R = H
Epothilone $H_2$ (13) R = Me

Epothilone C (14) $R^1$, $R^2$, $R^3$, $R^4$ = Me; R = H
Epothilone D (15) $R^1$, $R^2$, $R^3$, $R^4$, R = Me
Epothilone $C_1$ (16) $R^1$ = H; $R^2$, $R^3$, $R^4$ = Me; R = H
Epothilone $D_1$ (17) $R^1$ = H; $R^2$, $R^3$, $R^4$ = Me; R = Me
Epothilone $C_2$ (18) $R^2$ = H; $R^1$, $R^3$, $R^4$ = Me; R = H
Epothilone $D_2$ (19) $R^2$ = H; $R^1$, $R^3$, $R^4$ = Me; R = Me
Epothilone $C_3$ (20) $R^3$ = H; $R^1$, $R^2$, $R^4$ = Me; R = H
Epothilone $C_4$ (21) $R^4$ = H; $R^1$, $R^2$, $R^3$ = Me; R = H Epothilone $C_5$ (22) R = H
Epothilone $D_5$ (23) R = Me

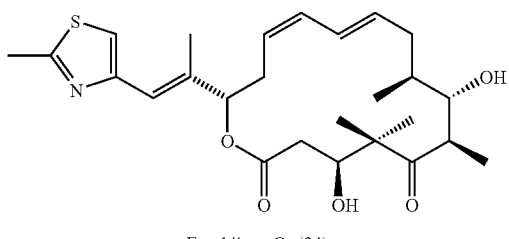

Epothilone C₆ (24)

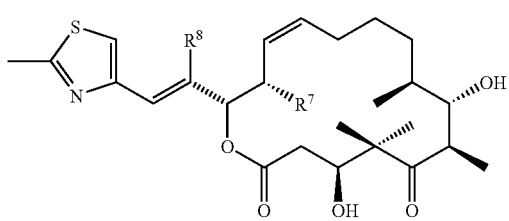

Epothilone C₇ (25) R⁷ = OH; R⁸ = Me
Epothilone C₈ (26) R⁸, R⁷ = H
Epothilone C₉ (27) R⁸ = CH₂OH; R⁷ = H

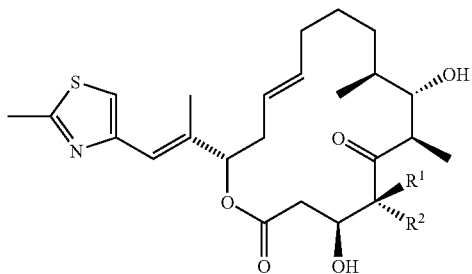

trans-Epothilone C₁ (28) R¹ = H; R² = Me
trans-Epothilone C₂ (29) R² = H; R¹ = Me

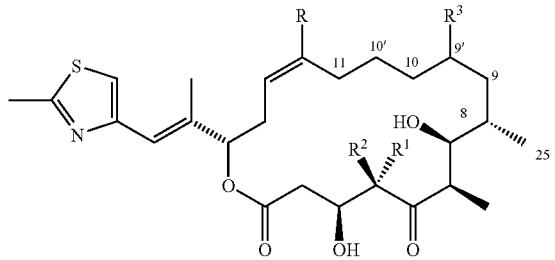

Epothilone I₁ (30) R, R³ = H; R¹, R² = Me
Epothilone I₂ (31) R = H; R¹, R², R³ = Me
Epothilone I₃ (32) R¹, R², R³ = Me
Epothilone I₄ (33) R², R = H; R¹, R³ = Me
Epothilone I₅ (34) R² = H; R¹, R³, R = Me
Epothilone I₆ (35) R¹ = H; R², R³, R = Me

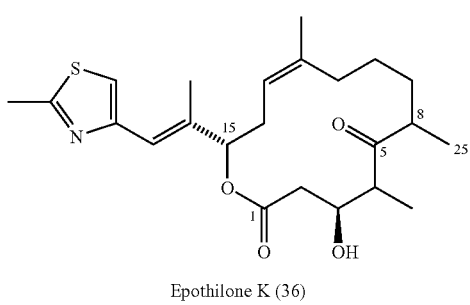

Epothilone K (36)

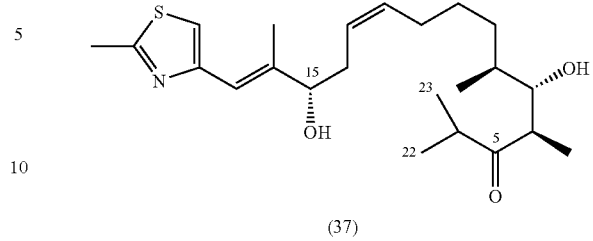

(37)

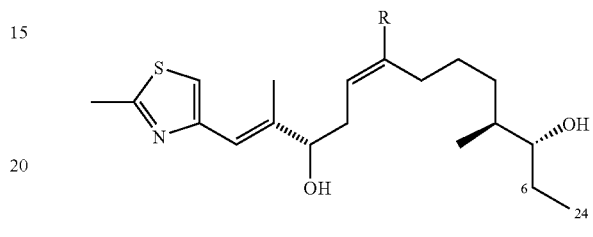

(38) R = H
(39) R = Me

Epothilone A₁ (5): colorless amorphous solid; [α]²²_D −69 (c 0.1, MeOH); UV (MeOH) λ_max nm (ε) 208 (19600), 247 (13600); IR (KBr) ν_max 3437, 2959, 2931, 2876, 1732, 1710, 1455, 1259, 978 cm⁻¹; ¹H NMR (CDCl₃, 400 MHz) δ 6.95 (1H, s, H-19), 6.60 (1H, bs, H-17), 5.68 (1H, dd, J=4.4, 4.0 Hz, H-15), 4.12 (1H, m, H-33), 3.71 (1H, m, H-7), 3.52 (1H, bs, 7-OH), 3.37 (1H, bd, J=7.5 Hz, 3-OH), 3.21 (1H, dq, J=7.7, 7.0 Hz, H-4), 3.02 (1H, ddd, J=9.2, 4.5, 2.8 Hz, H-13), 2.87 (1H, ddd, J=8.3, 4.5, 3.7 Hz, H-12), 2.78 (1H, dd, J=16.8, 4.3 Hz, H-2a), 2.70 (3 H, s, H-21), 2.66 (1H, dq, J=3.9, 7.0 Hz, H-6), 2.65 (1H, dd, J=16.8, 5.2 Hz, H-2b), 2.16 (1H, ddd, J=15.4, 4.4, 2.8 Hz, H-14 a), 2.12 (3H, bs, H-27), 1.91 (1H, ddd, J=15.4, 9.2, 4.0 Hz, H-14b), 1.63 (1H, m, H-10a), 1.62 (2H, m, H-11), 1.59 (1H, m, H-9a), 1.52 (1H, m, H-10b), 1.39 (1H, m, H-8), 1.35 (1H, m, H-9b), 1.211 (3H, d; J=7.0 Hz, H-2-3), 1.207 (3H, d, J=7.0 Hz, H-24), 0.89 (3H, d, J=6.9 Hz, H-25); EIMS m/z 479 [M]⁺ (21), 3322 (31), 306 (65), 304 (47), 168 (45), 166 (73), 164 (100), 151 (30), 140 (35); HREIMS m/z 479.2317 (calcd. for C₂₇H₄₁NO₅S, 479.2342).

Epothilone A₂ (6): colorless amorphous solid; [α]²²_D +12.0 (c 1.0, MeOH); UV (MeOH) λ_max nm (ε) 210 (15100), 248 (15500); IR (KBr) ν_max 3438, 2963, 2929, 2875, 1734, 1706, 1458, 1262, 981 cm⁻¹; ¹H NMR (CDCl₃, 400 MHz) δ 6.98 (1H, s, H-19), 6.63 (1H, bs, H-17), 5.40 (1H, dd, J=8.3, 3.4 Hz, H-15), 4.26 (1H, ddd, J=8.5, 4.8, 4.7 Hz, H-3), 3.85 (1H, dd, J=7.9, 2.6 Hz, H-7), 3.54 (1H, bs, 3-OH), 3.09 (1H, dq, J=4.8, 7.0 Hz, H-4), 3.01 (1H, ddd, J-8.3, 4.8, 4.6 Hz, H-13), 2.98 (1H, dq, J=7.9, 7.0 Hz, H-6), 2.89 (1H, ddd, J=6.7, 4.6, 4.4 Hz, H12), 2.68 (3H, s, H-21), 2.60 (1H, dd, J=15.1, 8.5 Hz, H-2a), 2.52 (1H, bs, 7-OH), 2.50 (1H, dd, J=15.1, 4.7 Hz, H-2b), 2.18 (1H, ddd, J=15.0, 4.8, 3.4 Hz, H-14a), 2.11 (3H, d, J=1.3 Hz, H-27), 1.82 (1H, ddd, J=15.0, 8.3, 8.1 Hz, H-14b), 1.63 (1H, m, H-8), 1.61 (2H, m, H-11a and H-10a), 1.46 (1H, m, H-11b), 1.39 (2H, m, H-9), 1.31 (1H, m, H-10b), 1.22 (3H, d, J=7.0 Hz, H-24), 1.15 (3H, d, J=7.0 Hz, H-22), 1.01 (3H, d, J=6.9 Hz, H-25); ¹³C NMR (CDCl₃, 100 MHz) δ 216.2 (s, C-5), 170.1 (s, C-1), 164.9 (s, C-20), 152.0 (s, C-18), 137.0 (s, C-16), 120.3 (d, C-17), 116.5 (d, C-19), 76.7 (d, C-15), 75.6 (d, C-7), 69.1 (d, C-3), 57.1 (d, C-12), 54.3 (d, C-13), 50.3 (d, C-4), 49.6 (d, C-6), 39.4 (t, C-2), 35.5 (d, C-8), 32.2 (t, C-14), 29.6 (t, C-9), 27.6 (t, C-11), 23.9 (t, C-10), 19.2 (q, C-21), 18.0 (q, C-25), 15.6 (q, C-27), 13.9 (q, C-24), 12.4 (q, C-22); EIMS m/z 479 [M]+ (18), 322 (38), 306 (78), 304 (59), 168 (48), 166 (96), 164 (100), 151 (33), 140 (38); HREIMS m/z 479.2318 (calcd. for $C_{27}H_{41}NO_5S$, 479.2342).

Epothilone $A_8$ (7): colorless amorphous solid; $[\alpha]^{22}D$ −76.2 (c 1.0, MeOH); UV (MeOH) $\lambda_{max}$ nm ($\epsilon$) 210 (15300), 248 (15500); IR (KBr) $\nu_{max}$ 3440, 2967, 2932, 2876, 1736, 1691, 1467, 1252, 979 cm$^{-1}$; $^1$H NMR (CDCl$_3$, 400 MHz) δ 6.95 (1H, s, H-19), 6.64 (1H, dd, J=15.6, 0.9 Hz, H-17), 6.52 (1H, dd, J=15.6, 6.6 Hz, H-16), 5.68 (1H, dddd, J=7.8, 6.6, 3.2, 0.9 Hz, H15), 4.11 (1H, ddd, J=10.1, 6.6, 3.5 Hz, H-3), 3.78 (1H, ddd, J=5.2, 3.2, 3.2 Hz, H-7), 3.66 (1H, d, 1=6.6 Hz, 3-01-1), 3.23 (1H, dq, 1=5.2, 6.9 Hz, 1-1-6), 3.08 (1H, ddd, J=7.3, 5.5, 4.1 Hz, H-13), 2.90 (1H, ddd, 1=6.6, 4.6, 4.1 Hz, H-12), 2.69 (3H, s, H-21), 2.52 (1H, dd, J=14.7, 10.1 Hz, H-2a), 2.44 (1H, bd, J=3.2 Hz, 7-OH), 2.41 (1H, dd, J=14.7, 3.5 Hz, H-2b), 2.10 (1H, ddd, J=15.0, 5.5, 3.2 Hz, H-14a), 1.90 (1H, ddd, J=15.0, 7.8, 7.3 Hz, H-14b), 1.711 (1H, m, H-8), 1.65 (1H, m, H-11a), 1.50 (1H, m, H-10a), 1.47 (1H, m, H-11b), 1.40(2K m, H-9), 1.39 (1H, m, H-10b), 1.33 (3H, s, H-2-3)), 1.16 (3H, d, J=6.9 Hz, H-24), 1.08 (3H, s, H-22), 0.98 (3H, d, J=7.0 Hz, H-25); $^{13}$C NMR (CDCl$_3$, 75 MHz) δ 220.3 (s, C-5), 170.7 (s, C-1), 166.5 (s, C-20), 152.2 (s, C-18), 128.4 (d, C-16), 125.9 (d, C-17), 116.4 (d, C-19), 75.0 (d, C-7), 73.6 (d, C-3), 72.7 (d, C-15), 57.3 (d, C-12), 54.1 (d, C-13), 52.6 (s, C-4), 43.8 (d, C-6), 38.9 (t, C-2), 36.3 (d, C-8), 32.5 (t, C-14), 30.3 (t, C-9), 26.7 (t, C-11), 24.0 (t, C-10), 21.3 (q, C-23), 21.0 (q, C-22), 19.3 (q, C-21), 17.1 (q, C-25), 14.5 (q, C-24); EIMS m/z 479 [M]+ XXX; HRDCIMS m/z 480.2401 (calcd. for $C_{25}H_{38}NO_6S$, 480.2401).

Epothilone $A_9$ (8): colorless amorphous solid; $[\alpha]^{22}_D$ −37.6 (c 0.5, MeOH); UV (MeOH) $\lambda_{max}$ nm ($\epsilon$) 211 (15500), 253 (14100); IR (KBr) $\nu_{max}$ 3423, 2965, 2932, 2877, 1736, 1690, 1463, 1249, 1014, 979 cm$^{-1}$; $^1$H NMR (CDCl$_3$, 400 MHz) δ 7.10 (1H, s, H-19), 6.72 (1H, dd, J=10.7, 4.3 Hz, 27-OH), 6.60 (1H, bs, H-17), 5.69 (1H, dd, J=11.6, 2.0 Hz, H-15), 5.59 (1H, d, J=6.6 Hz, 3-OH), 4.49 (1H, ddd, J=12.9, 4.3, 1.2 Hz, H-27a), 4.27 (1H, ddd, J=11.6, 6.6, 2.9 Hz, H-3), 4.11 (1H, ddd, J=12.9, 10.7, 1.0 Hz, H-27b), 3.71 (1H, ddd, J=4.8, 3.0, 2.8 Hz, H-7), 3.17 (1H, dq, J=3.0, 6.8 Hz, H-6), 3.04 (1H, ddd, J=9.7, 3.6, 2.2 Hz, H-13), 2.93 (1H, bs, 7OH), 2.91 (1H, ddd, J=9.7, 3.6, 2.7 Hz, H-12), 2.72 (3H, s, H-21), 2.48 (1H, dd, J=14.2, 11.6 Hz, H-2a), 2.11 (111, dd, J=14.2, 2.9 Hz, H-2b), 2.03 (1H, ddd, J=14.7, 2.2, 2.0 Hz, H-14a), 1.86 (1H, m, H-11 a), 1.85 (1H, m, -H-14b), 1.79 (1H, m, H-8), 1.52 (1H, m, H-10a), 1.37 (3H, m, H-9 and H-10b), 1.37 (3H, s, H-23), 1.36 (1H, m, H-11b), 1.19 (3H, d, J=6.8 Hz, H-24), 1.02 (3H, d, 1=7.1 Hz, H-25), 1.00 (3H, s, H-22); $^{13}$C NMR (CDCl$_3$, 75 MHz) δ 220.5 (s, C-5), 170.2 (s, C-1), 167.5 (s, C-20), 150.7 (s, C-18), 138.9 (s, C-16), 125.2 (d, C-17), 119.5 ((d, C19), 76.7 (d, C-15), 73.4 (d, C-7), 70.4 (d, C-3), 57.7 (d, C-12), 57.2 (t, C-27), 55.3 (d, C-13), 54.2 (s, C-4), 4i:3 (d, C-6),40.7 (t, C-2), 37.5 (d, C-8), 31.8 (t, C-14), 31.2 (t, C-9), 28.0 (t, C11), 23.7 (q, C-23), 23.2 (t, C-10), 19.2 (q, C-21), 16.58 (q, C-22), 15.8 (q, C-25), 13.5 (q, C-24); EIMS m/z 509 [M]+ (9), 491 (4), 322 (28), 321 (25), 180 (45), 167 (40), 166 (100), 165 (49), 154 (47), 138 (33); HREIMS m/z 509.2467 (calcd. for $C_{26}H_{39}NO_7S$, 509.2447).

Epothilone $B_{10}$ (9): colorless amorphous solid; $[\alpha]^{22}_D$ −27 (c 0.15, MeOH); UV (MeOH) $\lambda_{max}$ nm ($\epsilon$) 212 (15800), 247 (12500); IR (KBr) $\nu_{max}$ 3434, 2962, 2930, 2876, 2858, 1733, 1692, 1461, 1259, 1052, 981 cm$^{-1}$; $^1$H NMR (CDCl$_3$, 600 MHz) δ 6.99 (1H, s, H-19), 6.60 (1H, bs, H-17), 5.42 (1H, dd, J=8.0, 3.0 Hz, H-15), 4.25 (1H, ddd, J=9.5, 6.3, 2.8 Hz, H-3), 4.23 (1H, bs, 3-OH), 3.77 (1H, ddd, J=4.0, 3.9, 3.8 Hz, H-7), 3.30 (1H, dq, J=4.0, 6.9 Hz, H6), 3.01 (2H, q, J=7.6 Hz, H-21), 2.81 (1H, dd, J=7.7, 4.6 Hz, H-13), 2.68 (1H, bs, 7-OH), 2.54 (1H, dd, J=13.9, 9.5 Hz, H-2a), 2.36 (1H, dd, J=13.9, 2.8 Hz, H-2b), 2.11 (1H, ddd, J=15.3, 4.6, 3.0 Hz, H-14a), 2.09 (3H, s, H-27), 1.91 (1H, ddd, J=15.3, 8.0, 7.7 Hz, H-14b), 1.74 (1H, m, H-8), 1.73 (1H, m, H-11a), 1.51 (1H, m, H-10a), 1.41 (1H, m, H-11b), 1.39 (3H, t, J=7.6 Hz, H-28), 1.38 (3H, m, H-9 and H-10b), 1.37 (3H, s, H-23), 1.28 (3H, s, H-26),1.17 (3H, d, J=6.9 Hz, H-24), 1.09 (3H, s, H-22), 1.01 (3H, d, J=7.0 Hz, H-25); EIMS m/z 521 [M]+ (22), 449 (7), 350 (18), 334 (57), 248 (16), 234 (27), 196 (41), 182 (59), 180 (96), 178 (100), 166 (44), 154 (44); HREIMS m/z 521.2808 (calcd. for $C_{28}H_{43}NO_6S$, 521.2811).

Epothilone $G_1$ (10): colorless amorphous solid; $[\alpha]^{22}_D$ −39.7 (c 1.0, MeOH); UV (MeOH) $\lambda_{max}$ nm ($\epsilon$) 203 (15200), 236 (15100); IR (KBr) $\nu_{max}$3456, 2962, 2933, 2876, 1736, 1691, 1585, 1466, 1262, 980 cm$^{-1}$; $^1$H NMR (CDCl$_3$, 400 MHz) δ 7.47 (1H, s, H-19), 6.33 (1H, bs, H-17), 5.42 (1H, dd, J=8.3, 2.9 Hz, H-15), 4.11 (1H, ddd, J=10.1, 6.1, 3.4 Hz, H-3), 3.78 (1H, bddd, J=5.2, 3.5, 3.5 Hz, H-7), 3.63 (1H, bd, J=6.1 Hz, 3-OH), 3.21 (1H, dq, J=5.2, 7.0 Hz, H-6), 3.00 (1H, ddd, J=7.7, 4.8, 4.2 Hz, H-13), 2.88 (1H, ddd, J=7.1, 4.2, 4.2 Hz, H12), 2.53 (1H, dd, J=14.8, 10.1 Hz, H-2a), 2.51 (1H, bd, J=3.5 Hz, 7-OH), 2.43 (1H, dd, J=14.8, 3.4 Hz, H-2b), 2.43 (3H, s, H-21), 2.07 (1H, ddd, J=15.1, 4.8, 2.9 Hz, H-14a), 1.99 (3H, d, J=1.3 Hz, H-27), 1.86 (1H, ddd, J=15.1, 8.3, 7.7 Hz, H-14b), 1.71 (1H, m, H-8), 1.69 (1H, m, H-11a), 1.53 (1H, m, H-10a), 1.42 (1H, m, H-11b), 1.40 (3H, m, H-9 and H-10b), 1.34 (3H, s, H-23), 1.16 (3H, d, J=7.0 Hz, H-24), 1.09 (3H, s, H-22), 0.99 (3H, d, J=6.9 Hz, H25); $^{13}$C NMR, (CDCl$_3$, 100 MHz) δ 220.1 (s, C-5), 170.5 (s, C-1), 161.0 (s, C-20), 1374 (s, C18), 136.7 (s, C-16), 135.9 (d, C-19), 116.4 (d, C-17), 76.4 (d, C-15), 74.9 (d, C-7), 73.7 (d, C3), 57.4 (d, C-12), 54.4 (d, C-13), 52.6 (s, C-4), 43.8 (d, C-6), 38.8 (t, C-2),") 6.2 (d, C-8), 31.4 (t, C-14), 30.4 (t, C-9), 27.0 (t, C-11), 23.9 (t, C-10), 21.3 (q, C-23), 21.2 (q, C-22), 17.2 (q, C25), 15.8 (q, C-27), 14.4 (q, C-24), 13.8 (q, C-21); EIMS m/z 477 [M]+ (4), 405 (7), 290 (40), 152 (39), 150 (100), 14S (23), 124 (23); HREIMS m/z 477.2684 (calcd. for $C_{26}H_{39}NO_7$, 477.2727).

Epothilone $G_2$ (11): colorless amorphous solid; $[\alpha]^{22}_D$ −22.6 (c 1.0, MeOH); W (MeOH) $\lambda_{max}$ nm ($\epsilon$) 202 (21500), 236 (14800); IR (KBr) $\nu_{max}$3456, 2965, 2934, 2877, 1737, 1690, 1586, 1464, 1250, 980 cm$^{-1}$; $^1$H NMR (CDCl$_3$, 400 MHz) δ 7.48 (1H, s, H-19), 6.33 (1H, bs, H-17), 5.43 (1H, dd, J=7.1, 3.6 Hz, H-15), 4.12 (1H, ddd, J=9.9, 6.4, 3.4 Hz, H-3), 3.77 (1H, ddd, J=4.7, 4.4, 4.1 Hz, H-7), 3.83 (1H, bd, J=6.4 Hz, 3-OH), 3.30 (1H, dq, J=4.7, 6.9 Hz, H-6), 2.78 (1H, dd, J=7.0, 5.4 Hz, H-13), 2.54 (1H, dd, J=14.3, 9.9 Hz, H-2a), 2.51 (1H, bd, J=4.1 Hz, 7-OH), 2.44 (3H, s, H-21), 2.40 (1H, dd, J=14.3, 3.4 Hz, H-2b), 2.03 (1H, ddd, J=15.2, 5.4, 3.611z, H-14a), 2.00 (3H, d, J=1.3 Hz, H-27), 1.92 (1H, ddd, J=15.1, 7.1, 7.0 Hz, H-14b), 1.71 (1H, m, H-8), 1.68 (1H, m, H-11a), 1.51 (1H, m, H-10a), 1.42 (1H, M, H-11), 1.39 (3H, m, H-9 and H-10b), 1.35 (3H, s, H-23), 1.26 (3H, s, H-26), 1.16 (3H, d, J=6.9 Hz, H-24),1.07 (3H, s, H-22), 0.99 (3H, d, J=7.0 Hz, H-25); $^{13}$C NMR (CDCl$_3$, 100 MHz) δ 220.7 (s, C-5), 170.5 (s, C-1), 161.0 (s, C-20), 137.4 (s, C-18), 136.5 (s, C-16), 135.9 (d, C-19), 116.3 (d, C-17),76.6 (d, C-15), 74.6 (d, C-7),73.5 (d, C-3), 61.3 (s, C-12), 61.1 (d, C-13), 52.7 (s, C4),43.4 (d, C-6), 39.0 (t,-C-2), 36.5 (d, C-8), 32.0 (t, C-11), 31.8 (t, C-14), 30.8 (t, C-9), 22.8 (t, C-10), 22.9 (q, C-26), 21.0 (q, C-23), 20.8 (q, C-22), 17.2 (q, C-25), 15.9 (q, C-27), 14.1 (q, C-24), 13.8 (q, C-21); EIMS m/z 491 [M]+ (21), 419 (6), 320 (18), 304 (39), 166 (42), 152 (57), 150 (100), 149 (44), 148 (58), 124 (35), 109 (33); HREIMS m/z 491.2878 (calcd. for $C_{27}H_{41}NO_7$, 491.2883).

Epothilone $H_1$ (12): colorless amorphous solid; $[\alpha]^{22}_D$ −84.2 (c 0.2, MeOH); UV (MeOH) $\lambda_{max}$ nm ($\epsilon$) 203 (19600), 237 (12000); IR (KBr) $\nu_{max}$ 3436, 2933, 2880, 2860, 1734, 1688, 1585, 1251, 1007 cm$^{-1}$; $^1$H NMR (CDCl$_3$, 400 MHz) δ 7.47 (1H, s, H-19), 6.31 (1H, bs, H-17), 5.43 (1H, ddd, J=10.6, 10.2, 4.5 Hz, H-12), 5.36 (1H, dddd, J=10.6, 9.6, 5.0, 1.3 Hz, H-13), 5.30 (1H, dd, J=9.9, 2.0 Hz, H-15), 4.16 (1H, ddd, J=11.2, 5.3, 2.8 Hz, H-3), 3.73 (1H, ddd, J=3.9, 2.5, 2.3 Hz, H-7), 3.12 (1H, dq, J=2.3, 6.9 Hz, H-6), 2.92 (1H, d, J=2.5 Hz, 7-OH), 2.91 (1H, d, J=5.3 Hz, 7-OH), 2.66 (1H, ddd, J=15.1, 9.9, 9.6 Hz, H-14a), 2.50 (1H, dd, J=15.4, 11.2 Hz, H-2a), 2.43 (3H, s, H-21), 2.37 (1H, dd, J=15.4, 2.8 Hz, H-2b), 2.23 (1H, m, H-14b), 2.18 (1H, m, H-11a), 2.01 (1H, m, H-11), 2.08 (3H, d, J=1.3 Hz, H-27), 1.74 (1H, m, H-8), 1.65 (1H, m, H-10a), 1.33 (1H, m, H-9a), 1.31 (3H, s, H-23), 1.19 (1H, m, H-10b), 1.18 (1H, m, H-9b), 1.17 (3H, d, J=6.9 Hz, H-24), 1.08 (3H, s, H-22), 0.99 (3H, d, J=7.1 Hz, H-25); $^{13}$C NMR, see Table 1; EIMS m/z 461 [M]$^+$ (6), 310 (5), 274 (10), 273 (7), 171 (63), 152 (100), 148 (18), 111 (15); HREIMS m/z 461.2743 (calcd. for $C_{26}H_{39}NO_6$, 461.2777).

Epothilone $H_2$ (13): colorless amorphous solid; $[\alpha]^{22}_D$ −44.4 (c 0.25, MeOH); UV (MeOH) $\lambda_{max}$ nm ($\epsilon$) 203 (14500), 236 (12200); IR (KBr) $\nu_{max}$ 3436, 2967, 2935, 2880, 1734, 1690, 1586, 1251, 1007 cm$^{-1}$; $^1$H NMR (CDCl$_3$, 400 MHz) δ 7.46 (1H, s, H-19), 6.30 (1H, bs, H-17), 5.23 (1H, dd, J=9.8, 2.1 Hz, H-15), 5.12 (1H, dd, J=10.1, 5.3 Hz, H-13), 4.20 (1H, ddd, J=10.8, 5.7, 2.9 Hz, H-3), 3.71 (1H, ddd, J=3.8, 2.6, 2.6 Hz, H-7), 3.14 (1H, dq, J=2.6, 6.9 Hz, H-6), 2.93 (d, J=5.7 Hz, 3-OH), 2.90 (1H, bd, J=2.6 Hz, 7-OH), 2.62 (1H, ddd, J=15.1, 9.8, 9.8 Hz, H-14a), 2.46 (1H, dd, J=15.1, 10.8 Hz, H-2a), 2.43 (3H, s, H-21), 2.32 (1H, dd, J=15.1, 2.9 Hz, H-2b), 2.29 (1H, m, H-11a), 2.19 (1H, bd, J=15.1 Hz, H-14b), 1.97 (3H, d, J=1.3 Hz, H-27), 1.87 (1H, m, H-11b), 1.73 (1H, m, H-8), 1.67 (1H, m, H-10a), 1.65 (3H, bs, H-26), 1.32 (3H, s, H-23), 1.26 (2H, m, H-9), 1.24 (1H, m, H-10b), 1.18 (3H, d, J=6.9 Hz, H-24), 1.07 (3H, s, H-22), 1.00 (3H, d, J=7.0 Hz, H-25); $^{13}$C NMR (CDCl$_3$, 100 MHz) δ 220.6 (s, C-5), 170.3 (s, C-1), 161.0 (s, C-20), 138.6 (s, C-12), 138.4 (s, C-16), 137.5 (s, C-18), 135.6 (d, C-19), 120.8 (d, C-13), 115.8 (d, C-17), 78.9 (d, C-15), 74.3 (d, C-7), 72.7 (d, C-3), 53.3 (s, C-4), 42.0 (d, C-6), 39.6 (t, C-2), 38.6 (d, C-8), 32.4 (t, C-14), 31.9 (t, C-9), 31.6 (t, C-11), 25.6 (t, C-10), 23.0 (q, C-26), 22.8 (q, C-23), 18.8 (q, C-22), 16.1 (q, C-27), 15.9 (q, C-25), 13.8 (q, C-21), 13.6 (q, C-24); EIMS m/z 475 [M]$^+$ (11), 288 (9), 287 (5), 188 (7), 171 (32), 152 (100), 111 (10); HREIMS m/z 475.2913 (calcd. for $C_{27}H_{41}NO_6$, 475.2934).

Epothilone $C_1$ (16): colorless amorphous solid; $[\alpha]^{22}_D$ −114.0 (c 10.0, MeOH); UV (MeOH) $\lambda_{max}$ nm ($\epsilon$) 211 (16500), 248 (12500); IR (KBr) $\nu_{max}$ 3440, 2933, 2877, 2858, 1730, 1708, 1457, 1244, 981 cm$^{-1}$; $^1$H NMR (CDCl$_3$, 300 MHz) δ 6.96 (1H, s, H-19), 6.56 (1H, bs, H-17), 5.47 (1H, dd, J=9.2, 3.0 Hz, H-15), 5.43 (1H, m, H-12), 5.40 (1H, m, H-13), 4.40 (1H, ddd, J=6.2, 6.1, 6.1 Hz, H-3), 3.69 (1H, dd, J=5.7, 3.6 Hz, H-7), 3.01 (1H, dq, J=5.7, 6.9 Hz, H-6), 3.01 (1H, bs, 3-OH), 2.84 (1H, dq, J=5.2, 7.0 Hz, H-4), 2.68 (3H, s, H-21), 2.66 (1H, ddd, J=16.4, 9.2, 7.3 Hz, H-14a), 2.64 (1H, dd, J=15.9, 7.1 Hz, H-2a), 2.54 (1H, dd, J=15.9, 6.1 Hz, H-2b), 2.38 (1H, bd, J=16.4 Hz, H-14b), 2.35 (1H, bs, 7-OH), 2.07 (3H, bs, H-27), 2.03 (2H, m, H-11), 1.62 (1H, m, H-8), 1.53 (1H, m, H-8), 1.35 (1H, m, H-9a), 1.21 (1H, m, H-9b), 1.19 (3H, d, J=6.9 Hz, H-24), 1.14 (3H, d, J=6.9 Hz, H-23), 1.10 (1H, m, H-10b), 0.95 (3H, d, J=6.9 Hz, H-25); $^{13}$C NMR, see Table 1; EIMS m/z 463 [M]$^+$ (5), 324 (8), 290 (8), 204 (7), 168 (100), 164 (15), 139 (36); HREIMS m/z 463.2381 (calcd. for $C_{25}H_{37}NO_5S$, 463.2392).

Epothilone $D_1$ (17): colorless amorphous solid; $[\alpha]^{22}_D$ −118.6 (c 0.5, MeOH); UV (MeOH) $\lambda_{max}$ nm ($\epsilon$) 208 (18300), 249 (11900); IR (KBr) $\nu_{max}$ 3439, 2965, 2934, 2877, 1729, 1707, 1456, 1250, 980 cm$^{-1}$; $^1$H NMR (CDCl$_3$, 300 MHz) δ 6.98 (1H, s, H-19), 6.56 (1H, bs, H-17), 5.51 (1H, dd, J=9.5, 3.4 Hz, H-15), 5.16 (1H, dd, J=8.0, 4.2 Hz, H-13), 4.42 (1H, ddd, J=7.1, 6.3, 5.5 Hz, H-3), 3.70 (1H, dd, J=6.5, 2.9 Hz, H-7), 3.07 (1H, dq, J=6.5, 6.9 Hz, H-6), 2.95 (1H, dq, J=4.7, 7.0 Hz, H-4), 2.71 (3H, s, H-21), 2.69 (1H, dd, J=16.0, 6.3 Hz, H-2a), 2.64 (1H, m, H-14a), 2.59 (1H, dd, J=16.0, 7.1 Hz, H-2b), 2.46 (1H, bs, 3-OH), 2.38 (1H, bd, J=16.0 Hz, H-14b), 2.19 (1H, ddd, J=13.3, 8.6, 5.7 Hz, H-11a), 2.10 (3H, d, J=1.4 Hz, H-27), 2.02 (1H, bs, 7-OH), 1.91 (1H, ddd, J=13.3, 6.0, 6.0 Hz, H-11b), 1.68 (1H, m, H-10a), 1.66 (3H, bs, H-26), 1.53 (1H, m, H-8), 1.37 (1H, m, H-9a), 1.26 (1H, m, H-9b), 1.24 (3H, d, J=6.9 Hz, H-24), 1.19 (1H, m, H-10b), 1.14 (3H, d, J=7.0, H-23), 0.99 (3H, d, J=6.9 Hz, H-25); $^{13}$C NMR (CDCl$_3$, 100 MHz) δ 217.0 (s, C-5), 169.7 (s, C-1), 165.0 (s, C-20), 152.2 (s, C18), 1–38.5 (s, C-12), 137.7 (s, C-16), 120.7 (d, C-13), 120.1 (d, C-17), 116.3 (d, C-19), 78.8 (d, C-15), 77.2 (d, C-7), 67.7 (d, C-3), 52.1 (d, C-4), 46.5 (d, C-6), 40.6 (t, C-2), 37.6 (d, C-8), 32.3 (t, C-14), 31.8 (t, C-11), 29.5 (t, C-9), 25.5 (t, C-10), 23.1 (q, C-26), 19.2 (q, C-21), 15.5 (q, C27), 16.6 (q, C-25), 14.5 (q, C-24), 9.7 (q, C-23); EIMS m/z 477 [M]$^+$ (13), 304 (19), 303 (31), 218 (40), 204 (41), 168 (100), 164 (45), 157 (25), 139 (18); HREIMS m/z 477.2544 (calcd. for $C_{26}H_{39}NO_5S$, 477.2549).

Epothilone $C_2$ (18): colorless amorphous solid; $[\alpha]^{22}_D$ −11.6 (c 10.0, MeOH); UV (MeOH) $\lambda_{max}$ nm ($\epsilon$) 212 (15500), 249 (12100); IR (KBr) $\nu_{max}$ 3428, 2962, 2929, 2877, 2859, 1734, 1705, 1460, 1251, 9S2 cm$^{-1}$; $^1$H NM (CDCl$_3$, 300 MHz) δ 6.99 (1H, s, H-19), 6.66 (1H, bs, H-17), 5.55 (1H, ddd, J=10.4, 9.2, 6.1 Hz, H-12), 5.38 (1H, ddd, J=10.4, 9.3, 6.2 147, H-13), 5.22 (1H, dd, J=8.8, 2.8 Hz, H-15), 4.42 (1H, dddd, J=9.4, 5.6, 4.2, 4.1 Hz, H-3), 3.93 (1H, d, J=5.6 Hz, 3-OH), 3.86 (1H, m, H-7), 3.15 (1H, bs, 7-OH), 3.12 (1H, dq, J=4.2, 7.0 Hz, H-4), 3.00 (1H, dq, J=6.9, 7.0 Hz, H-6), 2.70 (3H, s, H-21), 2.62 (1H, dddd, J=15.1, 9.3, 8.8, 0.8 Hz, H-14a), 2.58 (1H, dd, J=15.4, 9.4 Hz, H-2a), 2.38 (1H, dd, J=15.4, 4.1 Hz, H-2b), 2.31 (1H, ddd, 0.1=15.1, 6.2, 2.8 Hz, H-14b), 2.08 (3H, d, J=1.3 Hz, H-27), 2.15 (1H, m, H-11a), 2.04 (1H, m, H-11b), 1.71 (1H, m, H-8), 1.59 (1H, m, H-10a), 1.43 (1H, m, H-9a), 1.31 (114, m, H-9b), 1.26 (3H, d, J=7.0 Hz, H-24), 1.15 (3H, d, J=7.0 Hz, H-23), 1.11 (1H, m, H-10b), 1.00 (3H, d, J=6.9 Hz, H-25); $^{13}$C NMR, see Table 1; EIMS m/z 463 [M]$^+$ (7), 324 (7), 306 (8), 290 (17), 168 (100), 164 (14), 139 (27); HREIMS m/z 463.2392 (calcd. for $C_{25}H_{37}NO_5S$, 463.2392).

Epothilone $D_2$ (19): colorless amorphous solid; $[\alpha]^{22}_D$ −12.5 (c 1.0, MeOH); UV (MeOH) $\lambda_{max}$ nm ($\epsilon$) 210 (15400), 248 (11200); IR (KBr) $\nu_{max}$ 3436, 2965, 2930, 2877, 1732, 1705, 1458, 1253, 980 cm$^{-1}$; $^1$H NMR (CDCl$_3$, 400 MHz) δ 6.97 (1H, s, H-19), 6.56 (1H, bs, H-17), 5.18 (IF, dd, J=7.9, 4.9 Hz, H-15), 5.18 (1H, ddd, J=9.6, 5.4, 1.0 Hz, H-13), 4.27 (1H, m, H-3), 3.88 (1H, dd, J=5.6, 4.6 Hz, H-7), 3.19 (1H, bs, 3-OH), 3.07 (1H, dq, J=4.3, 7.0 Hz, H-4), 2.95 (1H, dq, J=5.6, 7.0 Hz, H-6), 2.70 (3H, s, H-21), 2.62 (1H, dd, J=14.9, 7.8 Hz, H-2a), 2.56 (1H, ddd, J=14.7, 9.6, 7.9 Hz, H-14a), 2.43 (1H, dd, J=14.9, 5.6 Hz, H-2b), 2.38 (1H, bs, 7-OH), 2.26 (1H, ddd, J=14.5, 5.4, 4.9 Hz, H-14b), 2.19 (1H, ddd, J=13.0, 10.4, 5.4 Hz, H-11a), 2.10 (3H, d, 0.1=1.4 Hz, H-27), 1.95 (1H, ddd, J=13.0, 10.3, 5.3 Hz, H-l1b), 1.72 (1H, m, H-S), 1.68 (3H, bs, H-26), 1.61 (1H, m, H-10a), 1.39 (2H, m, H-9), 1.21 (1H, m, H-10b), 1.19 (3H, d, J=6.9 Hz, H-24),1.17 (3H, d, J=7.0, H-22),1.00 (3H, d, J=6.9 Hz, H-25J; $^{13}$C NMR (CDCl$_3$, 100 MHz) δ 216.8 (s, C-5), 170.4 (s, C-1), 164.9 (s, C-20), 152.3 (s, C-18), 139.8 (s, C-12), 137.5 (s, C-16), 120.5 (d, C-17), 119.2 (d, C-13), 116.3 (d, C-19), 80.0 (d, C-15), 74.3 (d, C-7), 69.7 (d, C-3), 48.6 (d, C-4), 48.4 (d, C-6), 39.9 (t, C-2), 36.6 (d, C-8), 32.2 (t, C-14), 32.7 (t, C-11), 30.9 (t, C-9), 26.0 (t, C-10), 23.6 (q, C-26), 19.2 (q, C-21), 15.4 (q, C-27), 17.1 (q, C-25), 12.4 (q, C-24), 12.7 (q, C-23); EIMS m/z 477 [M]+(22), 304 (19), 303 (17), 218 (22), 204 (25), 163 (100), 164 (28), 157 (31), 139 (21); HREIMS m/z 477.2545 (calcd. for C$_{26}$H$_{39}$NO$_5$S, 477.2549).

Epothilone C$_3$ (20): colorless amorphous solid; $[α]^{22}_D$ −62.1 (c 5.0, MeOH); UV (MeOH) λ$_{max}$ nm (ε) 212 (16200), 248 (12300); IR (KBr) ν$_{max}$ 3432, 2928, 2878, 2858, 1736, 1698, 1252, 1040 cm$^{-1}$; $^1$H NMR (CDCl$_3$, 300 MHz) δ 6.95 (1H, s, H-19), 6.56 (1H, bs, H-17), 5.44 (1H, ddd, J=10.9, 10.3, 5.4 Hz, H-12), 5.33 (1H, ddd, J=10.9, 9.3, 4.6 Hz, H-13), 5.23 (1H, dd, J=9.5, 2.2 Hz, H-15), 4.36 (1H, ddd, J=11.3, 5.6, 2.3 Hz, H-3), 4.04 (1H, d, J=5.6 Hz, 3-OH), 3.93 (1H, ddd, 0.1=9.5, 2.3, 1.4 Hz, H-7), 3.56 (1H, bd, J=2.3 Hz, 7-OH), 2.70 (1H, dd, J=18.0, 1.4 Hz, H-6a), 2.67 (3H, s, H-21), 2.61 (1H, ddd, J=15.3, 9.5, 9.3 Hz, H-14a), 2.38 (1H, dd, 0.1=14.3, 11.3 Hz, H-2a), 2.36 (1H, dd, J=18.0, 9.5 Hz, H-6b), 2.28 (1H, bd, J=15.3 Hz, H-14b), 2.12 (1H, m, H-11a), 2.06 (1H, dd, J=14.3, 2.3 Hz, H-2b), 2.03 (3H, d, J=1.3 Hz, H-27),1.96 (1H, m, H-11b), 1.75 (1H, m, H-8), 1.54 (1H, m, H-10a), 1.26 (1H, m, H-9a), 1.25 (3H, s, H-23),1.17 (1H, m, H-10b), 1.15 (1H, m, H-9b), 1.03 (3H, s, H-22),0.91 (3H, d, J=6.8 Hz, H-25); $^{13}$C NMR, see Table 1; EIMS m/z 463 [M]$^+$ (28), 290 (14), 168 (100), 164 (36), 157 (44), 151 (25), HREIMS m/z 463.2379 (calcd. for C$_{25}$H$_{37}$NO$_5$S, 463.2392).

Epothilone C$_4$ (21): colorless amorphous solid; $[α]^{22}_D$ −75.6 (c 1.0, MeOH); UV (MeOH)) λ$_{max}$ nm (ε) 212 (17200), 248 (12500); IR (KBr) ν$_{max}$ 3434, 2974, 2932, 2859, 1735, 1686, 1252, 1046 cm$^{-1}$; $^1$H NMR (CDCl$_3$, 300 MHz) δ 6.96 (1H, s, H-19), 6.60 (1H, bs, H-17), 5.43 (1H, m, H-12), 5.40 (1H, m, H-13), 5.26 (1H, dd, J=9.6, 2.3 Hz, H-15), 4.41 (1H, ddd, J=11.4, 5.8, 2.5 Hz, H-3 ), 3.78 (1H, m, H-7), 3.70 (1H, bs, 3-OH), 3.46 (1H, d, J=0.9 Hz, 7-OH), 3.01 (1H, dq, J=0.5, 7.0 Hz, H-6), 2.69 (3H, s, H-21), 2.66 (1H, ddd, J=15.3, 9.6, 8.8 Hz, H-14a), 2.47 (1H, dd, J=14.5, 11.4 Hz, H-2a), 2.29 (1H, m, H-14b), 2.25 (1H, dd, J=14.5, 2.5 Hz, H-2b), 2.24 (1H, m, H-11a), 2.07 (3H, d, J=1.4 Hz, H-27), 1.96 (1H, m, H-11b), 1.51 (2H, m, H-8), 1.44 (2H, m, H-10), 1.37 (2H, m, H-9), 1.32 (3H, s, H-23), 1.17 (3H, d, J=7.0 Hz, H-24), 1.07 (3H, s, H-22); $^{13}$C NMR, see Table 1; EIMS m/z 463 [M]$^+$ (7), 276 (15), 171 (33), 168 (100), 164 (23), 151 (22), 111 (13); HREIMS m/z 463.2373 (calcd. for C$_{25}$H$_{37}$NO$_5$S, 463.2392).

Epothilone C$_5$ (22): colorless amorphous solid; $[α]^{22}_D$ −158.2 (c 0.5, MeOH); UV (MeOH) λ$_{max}$ nm (ε) 205 (19500), 247 (12700); IR (KBr) ν$_{max}$ 3447, 2972, 2927, 1737, 1690, 1450, 1252, 1181, 936 cm$^{-1}$; $^1$H NMR (CDCl$_3$, 400 MHz) δ 6.93 (1H, s, H-19), 6.48 (1H, bs, H-17), 5.48 (1H, ddd, J=10.7, 6.2, 6.2 Hz, H-12), 5.39 (1H, m, H-13), 5.37 (1H, M, H-9), 5.34 (1H, dd, J=8.0, 2.3 Hz, H-15), 4.29 (1H, dd, J=6.0, 2.6 Hz, H-7), 4.09 (1H, ddd, J=10.8, 7.1, 2.9 Hz, H-3), 3.59 (1H, d, J=7.1 Hz, 3-OH), 3.17 (1H, dq, J=6.0, 6.9 Hz, H-6), 2.68 (3H, s, H-21), 2.54 (1H, ddd, J=15.2, 8.1, 8.0 Hz, H-14a), 2.44 (1H, bs, 7-OH), 2.42 (1H, dd, J=15.1, 2.9 Hz, H-2a), 2.41 (1H, ddd, J=15.2, 2.3, 2.3 Hz, H-14b), 2.34 (1H, dd, J=15.1, 10.8 Hz, H2b), 2.20 (1H, m, H-10a), 2.18 (2H, m, H-11), 2.12 (1H, m, H-10b), 2.06 (3H, bs, H-27), 1.67 13 (3H, bs, H-25), 1.27 (3H, s, H-23), 1.21 (3H, d, J=6.9 Hz, H-24), 1.15 (311, s, H-22); $^{13}$C NMR, see Table 1; EIMS m/z 475 [M]$^+$ (6), 392 (7), 304 (6), 288 (33), 204 (76), 171 (19), 168 (100), 164 (12); REIMS m/z 475.2380 (calcd. for C$_{26}$H$_{37}$NO$_5$S, 475.2392).

Epothilone D$_5$ (23): colorless amorphous solid; $[α]^{22}_D$ −150 (c 0.2, MeOH); UV (MeOH) λ$_{max}$ nm (ε) 205 (23300), 248 (13600); IR (KBr) ν$_{max}$ 3439, 2967, 2927, 1736, 1690, 1451, 1254, 1181, 987 cm$^{-1}$; $^1$H NMR (CDCl$_3$, 400 MHz) 5; 6.94 (1H, s, H-19), 6.51 (1H, bs, H-17), 5.34 (1H, bs, H-9), 5.29 (1H, dd, J=8.0, 2.4 Hz, H-15), 5.16 (1H, dd, J=8.2, 6.2 Hz, H-13), 4.30 (1H, bd, J=4.9 Hz, H-7), 4.19 (1H, ddd, J=10.8, 7.6, 3.0 Hz, H-3), 3.68 (1H, d, J=7.6 Hz, 3-OH), 3.17 (1H, dq, J=4.9, 7.0 Hz, H-6), 2.69 (3H, s, H-21), 2.65 (1H, d, J=2.1 Hz, 7-OH), 2.56 (1H, ddd, J=16.2, 8.2, 8.0 Hz, H-14a), 2.40 (1H, dd, J=15.0, 3.0 Hz, H-2a), 2.39 (1H, bd, J=16.2 Hz, H-14b), 2.34 (1H, dd, J=15.0, 10.8 Hz, H-2b), 2.25 (2H, m, H-10a and H-11a), 2.20 (1H, m, H-10b), 2.17 (1H, m, H-11b), 2.05 (3H, d, J=1.0 Hz, H-27),1.69 (3H, bs, H-25), 1.68 (3H, bs, H-26),1.29 (3H, s, H-23), 1.23 (3H, d, J=7.0 Hz, H-24), 1.16 (3H, s, H-22); $^{13}$C NMR, see Table 1; EIMS m/z 489 [M]$^+$ (4), 406 (4), 338 (7), 302 (13), 218 (35), 171 (10), 168 (100), 153 (20), 125 (10); HREIMS m/z 489.2536 (calcd. for C$_{27}$H$_{39}$NO$_5$S, 489.2549).

Epothilone C$_6$ (24): colorless amorphous solid; $[α]^{22}_D$ −205.2 (c 1.0, MeOH); UV (MeOH) λ$_{max}$ nm (ε) 218 (24600), 237 (28800); IR (KBr) ν$_{max}$ 3435, 2967, 2927, 2882, 1732, 1688, 1465, 1258, 988 cm$^{-1}$; $^1$H NMR (CDCl$_3$, 300 MHz) δ 6.97 (1H, s, H-19), 6.58 (1H, bs, H-17), 6.43 (1H, dd, 15.5, 10.8 Hz, H-11), 6.11 (1H, dd, J=10.8, 10.6 Hz, H-12), 5.75 (1H, ddd, J=15.5, 8.3, 5.6 Hz, H-10), 5.34 (1H, m, H-13), 5.34 (1H, dd, J=9.7, 2.4 Hz, H-15), 4.16 (1H, ddd, J=9.2, 4.9, 4.3 Hz, H-33), 3.74 (1H, ddd, J=2.2, 2.1, 1.7 Hz, H-7), 3.24 (1H, dq, J=2.1, 6.9 Hz, H-6), 3.06 (1H, d, J=2.2 Hz, 7-OH), 2.93 (1H, d, J=4.9 Hz, 3-OH), 2.78 (1H, dddd, J=14.1, 9.9, 9.7, 0.7, H-14a), 2.71 (3H, s, H-21), 2.48 (1H, m, H-9a), 2.47 (1H, dd, J=15.5, 9.2 Hz, H-2a), 2.40 (1H, dd, J=15.5, 4.3 Hz, H-2b), 2.38 (1H, bdd, J=14.1, 7.8 Hz, H-14b), 2.11 (3H, d, J=1.3 Hz, H-27), 1.96 (1H, m, H-8), 1.33 (3H, s, H-23), 1.11 (3H, d, J=6.9 Hz, H-24),1.06 (3H, s, H-22),1.05 (3H, d, J=6.8 Hz, H-25); $^{13}$C NMR, see Table 1; EIMS m/z 475 [M]$^+$ (13), 387 (2), 316 (4), 288 (15), 230 (16), 204 (9), 171 (18), 168 (100), 164 (14), 151 (17); HREIMS m/z 475.2361 (calcd. for C$_{26}$H$_{37}$NO$_5$S, 475.2392).

Epothilone C$_7$ (25): colorless amorphous solid; $[α]^{22}_D$ −XXX (c 2.0, MeOH); UV (MeOH) λ$_{max}$ nm (ε) XXX (XXX), XXX (XXX); IR (KBr) ν$_{max}$ XXX cm$^{-1}$; $^1$H NMR (CDCl$_3$, 400 MHz) δ 7.01 (1H, s, H-19),6.66 (1H, bs, H-17),5.59 (1H, ddd, J=11.1, 11.1, 3.8 Hz, H-12), 5.40 (1H, dd, J=11.1, 9.2, H-13), 5.03 (1H, d, J=9.3 Hz, H-15), 4.62 (1H, dd, J=9.3, 9.2 Hz, H-14), 4.18 (1H, bd, J=11.0 Hz, H-3), 3.72 (1H, bs, H-7),3.20 (1H, bs, 3-OH), 3.09 (1H, dq, J=1.9, 6.8 Hz, H-6), 3.00 (1H, bs, 7-OH), 2.69 (3H, s, H-21),2.47 (1H, dd, J=14.8, 11.0 Hz, H-2a), 2.32 (1H, dd, J=14.8, 2.6 Hz, H-2b), 2.27 (1H, m, H-11a), 2.19 (3H, bs, H-27), 2.13 (1H, m, H-11b), 1.76 (1H, m, H-8), 1.70 (1H, m, H-10a), 1.35 (1H, m, H-9a), 1.32 (3H, s, H-23 ), 1.23 (1H, m, H-9b), 1.21 (1H, m, H-10b), 1.18 (3H, d, J=6.8 Hz, H-24), 1.08 (3H, s, H-22), 1.00 (3H, d, J=6.9 Hz, H-25); EIMS m/z 493 [M]$^+$ XXX; HREIMS m/z 493.XXX (calcd. for C$_{26}$H$_{39}$NO$_6$S, 493.2498).

Epothilone C$_8$ (26): colorless amorphous solid; $[α]^{22}_D$ −75.2 (c 2.5, MeOH); UV (MeOH) λ$_{max}$ nm (ε) 210 (16803), 248 (17800); IR (KBr) ν$_{max}$3443, 2932, 2881, 1734, 1689, 1465, 1255, 1183, 976 cm$^{-1}$; $^1$H NMR (CDCl$_3$, 300 MHz) δ 6.93 (1H, s, H-19), 6.62 (1H, dd, J=15.6, 0.6 Hz, H-17), 6.49 (H, dd, J=15.6, 6.6 Hz, H-16), 5.52 (1H, dddd, J=9.5, 6.6, 2.8, 0.6 Hz, H-15), 5.42 (1H, m, H-12), 5.41 (1H, m, H-13), 4.13 (1H, ddd, J=11.0, 5.3, 2.8 Hz, H-3), 3.69 (1H, ddd, J=3.7, 2.8, 2.5 Hz, H-7), 3.11 (1H, dq, J=2.5, 6.8 Hz, H-6), 2.95 (1H, d, J=5.3 Hz, 3-OH), 2.90 (1H, d, J=2.8 Hz, 7-OH), 2.69 (3H, s, H-21), 2.67 (1H, ddd, 0.1=14.9, 9.5, 8.4 Hz, H-14a), 2.48 (1H, dd, J=15.6, 11.0 Hz, H-2a), 2.33 (1H, dd, J=15.6, 2.8 Hz, H-2b), 2.30 (1H, bd, J=14.9 Hz, H-14b), 2.14 (1H, m, H-11a), 2.03 (1H, m, H-11b), 1.71 (1H, m, H-8),1.63 (1H, m, H-10a), 1.31 (1H, m, H-9a), 1.29 (3H, s, H-23),1.17 (3H, d, J=6.8 Hz, H-24),1.16 (1H, m, H-10b), 1.14 (1H, m, H-9b), 1.05 (3H, s, H-22), 0.97 (3H, d, J=7.1 Hz, H-25); $^{13}$C NMR, see Table 1; EIMS m/z 463 [M]$^+$ (21), 310 (10), 276 (21), 171 (83), 154 (100), 150 (27), 111 (18); HREIMS m/z 463.2382 (calcd. for $C_{25}H_{37}NO_5S$, 463.2392).

Epothilone C$_9$, (27): colorless amorphous solid; $[\alpha]^{22}_D$ −93.4 (c 1.0, MeOH); UV (MeOH) $\lambda_{max}$ nm ($\epsilon$) 209 (15200), 254 (15700); IR (KBr) $\nu_{max}$ 3416, 2966, 2932, 1736, 1689, 1463, 1249, 1011 cm$^{-1}$; $^1$H NMR (CDCl$_3$, 400 MHz) δ 7.06 (1H, s, H-19), 6.65 (1H, bs, H-17), 6.56 (1H, dd, J=10.6, 4.4 Hz, 27-OH), 5.55 (1H, d, J=6.2 Hz, 3-OH),5.52 (1H, dd, J=11.6, 2.0 Hz, H-15), 5.44 (1H, dddd, J=11.2, 10.7, 3.1, 1.7 Hz, H-12), 5.35 (1H, dddd, J=11.0, 10.7, 3.9, 1.7 Hz, H-13),4.47 (11-1, ddd, J=12.5, 4.4, 1.3 Hz, H-27a), 4.35 (1H, ddd, J=11.7, 6.2, 2.6 Hz, H-3), 4.20 (1H, ddd, J=12.5, 10.6, 0.9 Hz, H-27b), 3.63 (1H, ddd, J=4.6, 1.8, 0.9 Hz, H-7), 3.24 (1H, d, J=1.8 Hz, 7-OH), 3.13 (1H, dq, J=0.9, 6.8 Hz, H-6), 2.80 (1H, ddd, J=14.8, 11.6, 11.0 Hz, H-14a), 2.71 (3H, s, H-21), 2.40 (1H, dd, J=14.4, 11.7 Hz, H-2a), 2.24 (1H, m, HI1a), 2.06 (1H, dd, J=14.4, 2.6 Hz, H-2b), 2.01 (1H, ddd; J=14.8, 3.9, 2.0 Hz, H-14b), 2.00 (1H, m, H-11b), 1.77 (1H, m, H-8),1.69 (1H, m, H-10a), 1.35 (1H, m, H-9a), 1.35 (3H, s, H23), 1.19 (1H, m, H-10b), 1.19 (3H, d, J=6.8 Hz, H-24), 1.18 (1H, m, H-9b), 1.01 (3H, d, J=7.1 Hz, H-25),0.98 (3H, H-22); $^{13}$C NMR, see Table 1; EIMS m/z 493 [M]$^+$ (17), 306'(64), 184 (50), 171 (30), 167 (38), 166 (100), 138 (12); HREIMS m/z 493.2502 (calcd. for $C_{26}H_{39}NO_6S$, 493.2498).

trans-Epothilone C$_1$, (28): colorless amorphous solid; $[\alpha]^{22}_D$ −84 (c 0.2, MeOH); UV (MeOH) $\lambda_{max}$ nm ($\epsilon$) 211 (17400), 248 (12900); 1R (KBr) $\nu_{max}$ 3433, 2961, 2933, 2879, 1730, 1708, 1457, 1251, 975 cm$^{-1}$; $^1$H NMR (CDCl$_3$, 600 MHz) δ 7.00 (1H, s, H-19),6.64 (1H, bs H17),5.45 (1H, ddd, J=15.2, 6.5, 6.5 Hz, H-12),5.42 (1H, dd, J=6.4, 3.7 Hz, H-15),5.35 (1H, dt, J=15.2, 7.1 Hz, H-13), 4.42 (1H, m, H-3),3.58 (1H, ddd, J=8.1, 7.9, 2.8 Hz, H-7),3.24 (1H, m, H-6), 3.14 (1H, dq, J=4.0, 6.9 Hz, H-6), 2.92 (1H, d, J=7.9 Hz, 7-OH), 2.71 (3H, s, H-21), 2.71 (2H, m, H-2), 2.53 (2H, m, H-14), 2.17 (1H, d, J=2.17 Hz, 3-OH), 2.11 (1H, m, H-11a), 2.06 (1H, bs, H-27), 1.93 (1H, m, H-11b), 1.68 (1H, m, H-9a), 1.65 (1H, m, H-10a), 1.33 (1H, m, H-8), 1.26 (3H, d, J=6.8 Hz, H-24), 1.16 (1H, m, H-10b), 1.12(3K d, J=6.9 Hz, H-22), 1.07 (1H, m, H-9b), 1.00 (3H, d, J=6.8 Hz, H-25); $^{13}$C NMR, see Table 1; EIMS m/z 463 [M]$^+$ (6),290 (21), 289 (20), 204 (23), 194 (19), 190 (22), 168 (100), 164 (48), 157 (14), 152 (19), 151 (17), 139 (15), 111 (18); HREIMS m/z 463.2371 (calcd. for $C_{25}H_{37}NO_5S$, 463.2392).

trans-Epothilone C$_2$ (29): colorless amorphous solid; $[\alpha]^{22}_D$ −3 (c 1.5, MeOH); UV (MeOH) $\lambda_{max}$ nm ($\epsilon$) 211 (15800), 248 (11900); IR (KBr) $\nu_{max}$ 3435, 2963, 2931, 2878, 1731, 1706, 1457, 1273, 979 cm$^{-1}$; $^1$H NMR (CDCl$_3$, 600 MHz) δ 6.99 (1H, s, H-19), 6.57 (1H, bs, H17), 5.56*(1H, ddd, J=15.1, 7.4, 7.0 Hz, H-12), 5.41 (1H, ddd, J=15.1, 7.0, 6.9 Hz, H-13), 5.41 (1H, dd, J=7.7, 2.8 Hz, H-15), 4.13 (1H, dddd, J=6.7, 6.2, 5.6, 5.1 Hz, H-3), 3.78 (1H, ddd, J=8.2, 6.5, 1.9 Hz, H-7), 3.18 (1H, d, J=5.6 Hz, 3-OH), 3.06 (1H, dq, J=8.2, 7.1 Hz, H-6),2.98 (1H, m, H-4), 2.71 (3H, s, H-21),2.64 (1H, dd, J=15.1, 6.7 Hz, H2a), 2.54 (1H, dd, J=15.1, 5.1 Hz, H-2b), 2.44 (2H, m, H-14),2.22 (1H, dddd, J=13.8, 7.0, 6.2, 2.9 Hz, H-11a), 2.10 (3H, d, J=1.1 Hz, H-27), 2.09 (~H, d, J=6.5 Hz, 7-OH), 1.88 (1H, dddd, J=13.8, 10.9, 7.4, 2.9 Hz, H-11b), 1.65 (1H, m, H-8), 1.63 (1H, m, H-10a), 1.56 (1H, dddd, J=12.7, 12.7, 3.9, 3.9 Hz, H-9a), 1.20 (3H, d, J=7.1 Hz, H-24), 1.15 (3H, d, J=7.0 Hz, H-23),1.13 (1H, m, H-10b), 1.04 (1H, m, H-9.b), 1.01 (3H, d, J=7.0 Hz, H-25); $^{13}$C NMR, see Table 1; EIMS m/z 463 [M]$^+$ (13), 290 (11), 190 (10), 168 (100), 164 (20), 157 (26), 139 (17); HREIMS m/z 463.2383 (calcd. for $C_{25}H_{37}NO_5S$, 463.2392).

Epothilone I$_1$, (30): colorless amorphous solid; $[\alpha]^{22}_D$ −XXX (c XXX, MeOH); UV (MeOH) $\lambda_{max}$ nm ($\epsilon$) XXX; IR (KBr) $\nu_{max}$ XXX cm$^{-1}$; $^1$H NMR (CDCl$_3$, 300 MHz) 6.96 (1H, s, H-19),6.54 (1H, bs, H-17),5.49 (Iii, ddd, J=10.3, 7.3, 7.3 Hz, H-12), 5.33 (1H, dd, J=8.3, 4.4 Hz, H-15),5.31 (1H, m, H-133),4.15 (1H, ddd, J=8.0, 5.0, 4.6 Hz, H-3), 3.80 (1H, m, H-7), 3.21 (1H, dq, J=6.0, 6.9 Hz, H-6),2.89 (1H, d, J=5.0 Hz, 3-OH); 2.70 (3H, s, H-21),2.65 (1H, ddd, J=15.8, 8.5, 8.3 Hz, H-14a), 2.42 (2H, m, H-2),2.35 (1H, m, H-14b), 2.27 (1H, bd, 0.1=3.3 Hz, 7-OH), 2.13 (1H, m, H-11a), 2.09 (3H, d, J=1.2 Hz, H-27),2.00 (1H, m, H-11b), 1.72 (1H, m, H-8), 1.40 (2H, m, H-10$_\beta$), 1.37 (1H, m, H-9$_\beta$a), 1.36 (2H, m, H-9$_a$), 1.32 (3H, s, .H-23),1.27 (3H, m, H-9$_\beta$b and H-10$_a$), 1.13 (3H, d, J=6.9 Hz, H-24), 1.09 (3H, s, H-22),0.94 (3H, d, J=6.9 Hz, H-25); $^{13}$C NMR (CDCl$_3$, 75 MHz) δ 221.3 (s, C-5), 171.1 (s, C-1), 164.8 (s, C-20), 152.4 (s, C-18), 137.4 (s, C-16), 133.8 (d, C-12),124.6 (d, C-13), 120.0 (d, C-17), 116.2 (d, C-19), 78.8 (d, C-15), 74.9 (d, C-7), 74.7 (d, C-3), 51.6 (s, C4), 43.7 (d, C-6), 38.9 (t, C-2), 34.3 (d, C-8), 31.6 (t, C-14), 29.3 (t, C-9$_a$), 28.6 (t, C-10$_\beta$), 28.2 (t, C-10$_a$), 26.6 (t, C-11), 24.8 (t, C-9$_\beta$), 23.6 (q, C-22), 19.3 (q, C23), 19.3 (q, C-21), 16.5 (q, C-25), 15.5 (q, C:27), 13.7 (q, C-24); EIMS m/z 505 [M]$^+$ XXX; HREIMS m/z 505.XXX (calcd. for $C_{28}H_{43}NO_5S$, 505.XXX).

Epothilone I$_2$, (31): colorless amorphous solid; $[\alpha]^{22}_D$ −XXX (c XXX, MeOH); UV (MeOH) $\lambda_{max}$ nm ($\epsilon$) XXX; IR (KBr) $\nu_{max}$ XXX cm$^{-1}$; $^1$H NMR (CDCl$_3$, 300 MHz) α 6.95 (1H, s, H-19), 6.53 (1H, bs, H-17), 5.40 (1H, m, H-12), 5.38 (1H, dd, J=9.8, 3.3 Hz, H-15), 5.37 (1H, m, H-133),4.21 (1H, ddd, 0.1=8.6, 3.8, 3.6 Hz, H-3),3.85 (1H, ddd, J=8.5, 5.8, 2.2 Hz, H7), 3.18 (1H, dq, J=8.5, 7.0 Hz, H-6),2.70 (3H, s, H-21),2.65 (1H, ddd, J=15.2, 9.8, 9.0 Hz, H-14a), 2.51 (1H, d, J=3.6 Hz, 3-OH), 2.37 (2H, m, H-2), 2.32 (1H, bd, J=15.2 Hz, H-14b), 2.09 (3H, d, J=1.3 Hz, H-27),2.07 (2H, m, H-11), 1.78 (1H, m, H-8), 1.65 (1H, d, J=5.8 Hz, 7-OH), 1.57 (1H, m, H-10$_\alpha$a), 1.44 (1H, m, H-10$_\alpha$a), 1.42 (1H, m, H-9$_\beta$, 1.32 (3H, s, H-23), 1.21 (1H, m, H-10$_\beta$b), 1.17 (3H, d, J=7.0 Hz, H-24),1.13 (2H, m, H-9$_\alpha$),1.06 (3H, s, H-22), 0.95 (3H, d, J=7.0 Hz, H-25$_\alpha$), 0.91 (3H, d, J=6.5 Hz, H-25$_\beta$), 0.68 (1H, m, H-10.b); $^{13}$C NMR (CDCl$_3$, 100 MHz) δ 220.4 (s, C-5),171.3 (s) (s, C-1), XXX (s, C-20),152.4 (s, C-18),137.6 (s, C-16), 13)4.5 (d, C-12),125.3 (d, C-13), 119.6 (d, C-17),116.2 (d, C-19),78.6 (d, C-15),77.2 (d, C-7),75.0 (d, C-3), 51.0 (s, C-4),44.6 (d, C-6),38.2 (t, C-2),36.9 (t, C-9$_\alpha$),34.5 (t, C-10$_\alpha$) 32.6 (d, C-8), 32.0 (t, C-14), 30.0 (d, C-9$_\beta$), 27.4 (t, C-11), 26.6 (t, C-10p), 25.0 (q, C-22), 21.5 (q, C-25$_\beta$), 19.3 (q, C-21),17.9 (q, C-25$_\alpha$),17.7 (q, C-23),15.8 (q, C-24),15.6 (q, C-27); EIMS m/z 519 MV XXX; HREIMS, n/. 519.XXX (calcd. for $C_{29}H_{45}NO_5S$, 519.XXX).

Epothilone I$_3$ (32): colorless amorphous solid; $[\alpha]^{22}_D$ −XXX (c XXX, MeOH); UV (MeOH) $\lambda_{max}$ nm ($\epsilon$) XXX; IR (KBr) $\nu_{max}$ XXX cm$^{-1}$; $^1$H NMR (CDCl$_3$, 400 MHz) δ 6.95 (1H, s, H-19),6.52 (1H, bs, H-17),5.32 (1H, dd, J=9.1, 3.0 Hz, H-15), 5.08 (1H, dd, J=8.~,3.9 Hz, H-13), 4.13 (1H, ddd, J=9.4, 4.3, 3.2 Hz, H-3),3.81 (1H, m, H-7), 3.18 (1H, dq, J=6.8, 7.0 Hz, H-6), 2.83 (1H, d, J=4.3 Hz, 3-OH), 2.70 (3H, s, H-21), 2.61 (1H, ddd, J=15.8, 9.1, 8.5 Hz, H-14 a), 2.43

(1H, dd, J=14.0, 3.2 Hz, H-2a), 2.38 (2H, dd, J=14.0, 9.4 Hz, H-2b), 2.30 (1H, bd, J=15.8 Hz, H-14b), 2.16 (1H, ddd, J=14.1, 8.3, 7.4 Hz, H-11a), 2.08 (3H, d, J=1.0 Hz, H-27), 1.99 (1H, d, J=4.7 Hz, 7-OH), 1.92 (1H, ddd, J=14.1, 6.3, 6.3 Hz, H-1 Ib), 1.82 (1H, m, H-8), 1.67 (3H, s, H-26), 1.51 (1H, m, H-10$_\beta$a), 1.40 (1H, m, H-9$_\beta$), 1.33 (1H, m, H-10$_\beta$b), 1.31 (3H, s, H-23), 1.27 (1H, M H-10$_\alpha$a), 1.23 (1H, m, H-9$_\alpha$a), 1.16 (3H, d, J=7.0 Hz, H-24), 1.10 (1H, m, H-9$_\alpha$b), 1.07 (3H, s, H-22), 0.95 (3H, d, J=7.0 Hz, H-25$_\alpha$), 0.92 (3H, d, J=6.5 Hz, H-25$_\beta$), 0.75 (1H, m, H-10$_\alpha$b); EIMS m/z 533 M$^+$ XXX; HREIMS m/z 533.XXX (calcd. for $C_{30}H_{47}NO_5S$, 533.XXX).

Epothilone I$_4$ (33): colorless amorphous solid; $[\alpha]^{22}_D$ –XXX (c XXX, MeOH); UV (MeOH) $\lambda_{max}$ nm ($\epsilon$) XXX; IR (KBr) $\nu_{max}$XXX cm$^{-1}$; $^1$H NMR (CDCl$_3$, 400 MHz) δ 6.95 (1H, s, H-19), 6.53 (1H, bs, H-17), 5.47 (1H, dt, J=11.1, 5.8 Hz, H-12), 5.33 (1H, ddd, J=9.2, 3.9, 0.5 Hz, H-15), 5.33 (1H, m, H-13), 4.09 (1H, dddd, J=9.6, 8.1, 4.5, 3.3 Hz, H-3), 3.83 (1H, m, H-7), 3.57 (1H, bs, 3-OH), 2.89 (1H, dq, J=7.4, 7.1 Hz, H-6), 2.83 (1H, dq, J=8.1, 7.1 Hz, H-4),2.70 (3H, s, H-21),2.64 (1H, m, H-14a), 2.42 (1H, dd, J=14.2, 3.3 Hz, H-2a), 2.43 (1H, dd, J=14.2, 9.6 Hz, H-2b), 2.30 (1H, m, H-14b), 2.10 (3H, d, J=1.3 Hz, H-27),2.09 (2H, m, H-11), 1.81 (1H, m, H-8),1.74 (1H, bd, J=5.6 Hz, 7-OH), 1.53 (1H, m, H-10$_\beta$a), 1.49 (1H, m, H-9$_\beta$), 1.47 (1H, m, H-10$_\alpha$a), 1.27 (1H, m, H-10$_\beta$b), 1.24 (1, m, H-9$_\alpha$a) 1.17 (3H, d, J=7.1 Hz, H-23),1.14 (1H, m, H-9$_\alpha$b) 1.08 (3H, d, J=7.1 Hz, H-24), 0.97 (3H, d, J=6.9 Hz, H-25$_\alpha$), 0.91 (3H, d, J=6.5 Hz, H-25$_\beta$), 0.79 (1H, m, H-10$_\alpha$b); $^{13}$C NMR (CDCl$_3$, 100 MHz) δ 217.0 (s, C-5), 170.8 (s, C-1), 164.8 (s, C-20), 152.4 (s, C-18), 137.1 (s, C-16), 134.6 (d, C-12), 124.7 (d, C-13), 120.2 (d, C-17),116.4 (d, C-19),78.7 (d, C-15), 76.4 (d, C-7),71.3 (d, C-3), 50.7 (d, C4), 50.1 (d, C-6), 40.7 (t, C-2), 38.5 (t, C-9$_\alpha$), 35.5 (t, C-10$_\alpha$), 33.4 (d, C-8), 31.8 (t, C-14), 30.0 (d, C-9$_\beta$), 27.2 (t, C-11), 26.7 (t, C-10$_\beta$), 21.4 (q, C-25$_\beta$), 19.3 (q, C-21), 18.2 (q, C-25$_\alpha$), 15.4 (q, C-27),14.4 (q, C-24), 13.1 (q, C-23); EIMS m/z 505 [M]$^+$ XXX; HREIMS m/z 505.XXX (calcd. for $C_{28}H_{43}NO_5S$, 505.XX.X).

Epothilone I$_5$, (34): colorless amorphous solid; $[\alpha]^{22}_D$ –XXX (c XXX, MeOH); UV (MeOH)) $\lambda_{max}$ nm ($\epsilon$) XXX; IR (KBr) $\nu_{max}$XXX cm$^{-1}$; $^1$H NMR (CDCl$_3$, 400 MHz) δ 6.97 (1H, s, H-19), 6.52 (1H, bs, H-17), 5.32 (1H, dd, J=7.1, 6.2 Hz, H-15), 5.03 (1H, dd, J=8.4, 5.0 Hz, H-13), 4.05 (1H, dddd, J=7.5, 7.2, 5.9, 4.6 Hz, H-3), 3.91 (1H, m, H-7), 3.17 (1H, d, J5.9 Hz, 3-OH), 2.94 (1H, d q, J=7.2, 7.1 Hz, H4), 2.87 (1H, dq, J=6.5, 6.9 Hz, H-6), 2.70 (3H, s, H-21), 2.62 (1H, dd, J=14.6, 4.6 Hz, H-2a), 2.60 (1H, M, H-14a), 2.53 (1H, dd, J=14.6, 7.5 Hz, H-2b), 2.31 (1H, m, H-14b), 2.10 (3H, d, J=1.1 Hz, H-27), 2.10 (1H, M, H-11a), 2.02 (1H, m, H-IIb), 1.97 (1H, bd, 1=5.6 Hz, 7-OH), 1.84 (1H, m, H-8), 1.66 (3H, s, H-26), 1.55 (1H, m, H-9$_\beta$) 1.49 (1H, m, H-10$_\beta$a), 1.39 (1H, m, H-10$_\beta$b), 1.33. (1H, m, H-10$_\alpha$a), 1.31 (1H, m, H-9$_\alpha$), 1.15 (3H, d, J=7.1 Hz, H-23), 1.12 (1H, m, H-9$_\alpha$b), 1.11 (3H d, J=6.9 Hz, H-24), 0.97 (3H, d, J=6.9 Hz, H-25$_\alpha$), 0.94 (1H, m, H-10$_\alpha$b), 0.93 (3H, d, J=6.6 Hz, H-25$_\beta$); EIMS m/z 519 [M]$^+$ XXX; HREIMS ink 519.XXX (calcd. for $C_{29}H_{45}NO_5S$, 519.XXX.

Epothilone I$_6$ (35): colorless, amorphous solid; $[\alpha]^{22}_D$ –XXX (c XXX, MeOH); UV (MeOH) $\lambda_{max}$ nm ($\epsilon$) XXX; IR (KBr) $\nu_{max}$XXX cm$^{-1}$; $^1$H NMR (CDCl$_3$, 400 MHz) δ 6.97 (1H, s, H-19),6.52 (1H, bs, H-17),5.24 (1H, dd, J=6.9, 6.9 Hz, H-15),5.02 (1H, dd, J=8.8, 5.2 Hz, H-13),4.22 (1H, tdd, J=6.1, 5.6, 4.8 Hz, H-3),3.76 (1H, mdd, J=6.1, 5.7, 5.6 Hz, H-7), 3.13 (1H, d, J=5.6 Hz, 3-OH), 3.05 (1H, dq, J=4.8, 7.0 Hz, H-4), 2.79 (1H, dq, J=5.6, 6.9 Hz, H-6),2.70 (3H, s, H-21), 2.62 (1H, m, H-14a), 2.57 (2H, d, J=6.1 Hz, H-2a), 2.30 (1H, m, H-14b), 2.08 (3H, d, J=1.0 Hz, H-27), 2.02 (2H, m, H-11), 1.73 (1H, d, J=6.1 Hz, 7-OH), 1.69 (1H, m, H-8), 1.66 (3H, s, H-26), XXX (H-9$_\alpha$, H-9$_\beta$, H-10$_\alpha$, H-10$_\beta$), 1.21 (3H, d, J=7.0. Hz, H-22), 1.16 (3H, d, J=6.9 Hz, H-24), 0.94 (3H, d, J=6.9 Hz, H-25$_\alpha$), 0.91 (3H, d, J=6.4 Hz, H-25$_\beta$); EIMS m/z 519 [M]$^+$ XXX; HREIMS m/z 519.XXX (calcd. for $C_{29}H_{45}NO_5S$, 519.XXX).

Epothilone K (36): colorless amorphous solid; $[\alpha]^{22}_D$ –7 (c 0.08, MeOH); UV (MeOH) $\lambda_{max}$ nm ($\epsilon$) 212 (16700), 248 (12500); IR (KBr) $\nu_{max}$3431, 2963, 2927, 2856, 1731, 1712, 1262, 1093, 1021, 802 cm$^{-1}$; $^1$H NMR (CDCl$_3$, 300 MHz) δ 6.95 (1H, s, H-19), 6.51 (1H, bs, H-17), 5.49 (31H, m, H-15, H-13, and H-12), 4.04 (1H, dddd, J=7.9, 7.6, 6.9, 3.3 Hz, H-3), 3.36 (1H, dq, J=6.9, 6.8 Hz, H-6), 2.83 (1H, d, J=7.6 Hz, 3-OH), 2.75 (1H, ddd, J=16.1, 6.6, 3.4 Hz, H-14a), 2.74 (1H, dd, J=15.3, 3.3 Hz, H-2a), 2.71 (3H, s, H-21), 2.58 (2H, m, H-14b and H-8), 2.50 (1H, dd, J=15.3, 7.9 Hz, H-2b), 2.29 (1H, m, H-11a), 2.10 (1H, m, H-11b), 2.09 (311, d, J=0.7 Hz, H-27), 1.78 (1H,-m, H-9a), 1.65 (1H, m, H-10a), 1.48 (1H, m, H-10b), 1.18 (1H, m, H-9b), 1.15 (3H, d, J=6.8 Hz, H-22), 1.03 (3H, d, J=6.5 Hz, H-25); EIMS m/z 405 [M]$^+$ (38), 317 (12), 260 (9), 232 (10), 204 (14), 190 (16), 168 (100), 164 (30), 151 (28); HREIMS m/z 405."X (calcd. for $C_{26}H_{39}NO_5S$, 405.XXX).

(37): colorless amorphous solid; $[\alpha]^{22}_D$ –27.5 (c 0.4, MeOH); UV (MeOH) $\lambda_{max}$ nm ($\epsilon$) 211 (16100), 247 (12100); IR (KBr) $\nu_{max}$3431, 2967, 2929, 2875, 1704, 1462, 1381, 1010 cm$^{-1}$; $^1$H NMR (CDCl$_3$, 400 MHz) δ 6.94 (1H, s, H-19), 6.55 (1H, bs, H-17),5.56 (1H, dtt, J=10.8, 7.3, 1.4 Hz, H-12),5.39 (1H, dtt, J=10.8, 7.3, 1.4 Hz, H-13), 4.17 (1H, t, J=6.6 Hz, H-15), 3.50 (1H, ddd, J=8.7, 2.6, 2.6 Hz, H-7), 3.10 (1H, d, J=2.6, 7-OH), 2.90 (1H, dq, J=2.6, 7.2 Hz, H-6), 2.77 (1H, sep, J=6.9 Hz, H-4), 2.70 (3H, s, H-21), 2.40 (2H, m, H-14), 2.07 (2H, m, H-11), 2.04 (3H, d, J=1.1 Hz, H-27),1.78 (1H, bs, 15-OH), 1.74 (1H, m, H-9a), 1.50 (1H, m, H-8), 1.46 (1H, m, H-10a), 1.27 (1H, m, H-10b), 1.11 (1H, m, H-9b), 1.094 (3H, d, J=6.9 Hz, H-23), 1.089 (3H, d, J=6.9 Hz, H-22), 1.08 (3H, d, J=7.2 Hz, H-24), 0.82 (3H, d, J=6.7 Hz, H-25); $^{13}$C NMR (CDCl$_3$, 100 MHz) δ 220.5 (s, C-5), 164.6 (s, C-20), 152.9 (s, C-18), 141.5 (s, C-16), 133.4 (d, C-12), 125.0 (d, C-13), 119.2 (d, C-17), 115.6 (d, C-19), 77.2 (d, C-15), 74.9 (d, C-7), 44.9 (d, C-6), 40.0 (d, C-4), 35.5 (d, C-8), 33.5 (t, C-14), 32.3 (t, C-9), 27.9 (t, C-11), 26.9 (t, C-10), 19.2 (q, C-21), 18.6 (q, C-23), 18.1 (q, C-22), 15.6 (q, C-25), 14.4 (q, C-27), 9–3 (q, C-24); EIMS m/z 407 [M]$^+$ (0.1), 204 (0.8), 168 (100), 140 (3.4); HREIMS m/z 407.XXX (calcd. for $C_{23}H_{37}NO_3S$, 407.XXX).

(38): colorless amorphous solid; $[\alpha]^{22}_D$ +25.0 (c 0.5, MeOH); UV (MeOH) $\lambda_{max}$ nm ($\epsilon$) 212 (17700), 247 (13400); IR (KBr) $\nu_{max}$3427, 2971, 2933, 2878, 2858, 1709, 1457, 1377, 1186, 1023 cm$^{-1}$; $^1$H NMR (CDCl$_3$, 300 MHz) δ 6.95 (1H, s, H-19), 6.55 (1H, bs, H-17), 5.52 (1H, dtt, J=10.9, 7.2, 1.4 Hz, H-12), 5.39 (1H, dtt, J=10.9, 7.1, 1.2 Hz, H-13), 4.18 (1H, ddt, J=3.4, 0.4, 6.7 Hz, H-15), 2.71 (3H, s, H-21), 2.51 (1H, bq, J=6.8 Hz, H-8), 2.48 (1H, dq, J=17.7, 7.4 Hz, H-6a), 2.41 (1H, dq, 1=17.7, 7.2 Hz, H-6b), 2.39 (2H, ddd, J=7.1, 6.7, 1.4 Hz, H-14), 2.06 (2H, ddt, 7.2, 1.2, 7.0 Hz, H-11), 2.05 (3H, d, J=1.4 Hz, H-27), 1.81 (1H, d, J=3.4 Hz, 15-01-1), 1.66 (1H, m, H-9a), 1.32 (1H, m, H-9b), 1.31 (2H, m, H-10), 1.06 (3K d, J=6J Hz, H-25), 1.04 (3H, dd, J=7.4, 7.2 Hz, H-24); $^{13}$C NMR (CDCl$_3$, 75 MHz) δ 215.3 (s, C-7), 164.6 (s, C-20),152.9 (s, C-18),141.5 (s, C-16),132.7 (d, C-12),125.3 (d, C-13),119.2 (d, C-17), 115.6 (d, C-19),77.2 (d, C-15),46.0 (d, C-8),34.3 (t, C-14), 33.5 (t, C-6), 32.7 (t, C-9),27.5 (t, C-11), 27.3 (t, C-10), 19.2 (q, C-21),16.5 (q, C-25),14.4 (q, C-27), 7.8 (q, C-24); EIMS m/z 335 [M]⁺ (2),317 (4),170 (27), 169 (67), 168 (100), 140 (20); HREIMS m1z 335.1912 (calcd. for $C_{19}H_{29}NO_2S$, 335.1919).

(39): colorless amorphous solid; $[\alpha]^{22}_D$ +26.4 (c 0.27, MeOH); UV (MeOH) $\lambda_{max}$ nm ($\epsilon$) 203 (19100), 244 (12500); IR (KBr) $v_{max}$3430, 2970, 2934, 2877, 1710, 1458, 1377, 1184 cm⁻¹; ¹H NMR (CDCl₃, 400 MHz) δ 6.94 (1H, s, H-19),6.55 (1H, bs, H-17), 5.17 (1H, t, J=7.3 Hz, H-13), 4.13 (1H, m, H-15), 2.70 (3H, s, H-21), 2.51 (1H, bq, J=6.8 Hz, H-8), 2.47 (1H, dq, J=17.7, 7.2 Hz, H-6a), 2.41 (1H, dq, J=17.7, 7.2 Hz, H-6b), 2.33 (2H, bdd, J=7.3, 6.8 Hz, H-14),2.05 (3H, d, J=1.2 Hz, H-27),2.03 (2H, m, H-11), 1.71 (1H, d, J=3.2 Hz, 15-OH), 1.69 (3H, d, J=1.3 Hz, H-26),1.62 (1H, m, H-9a), 1.32 (3H, m, H-10 and H-9b), 1.06 (3H, d, J=6.9 Hz, H-25), 1.03 (3H, t, J=7.2 Hz, H-24); EIMS m/z 349 [M]⁺ (0.7), 331 (1.7), 168 (100), 140 (5.1); HREIMS m/., 349.XXX (calcd. for $C_{20}H_{31}NO_2S$, 349.XXX).

TABLE 1

Activity of epothilones and compounds (1) to (39) against mouse fibroblasts (L929, IC 50/ng/ml)

| Structural type | Aγ | Bγ | Cγ | Dγ | trans Cγ |
|---|---|---|---|---|---|
| Starting epothilone | (1) 4 | (2) 1–2 | (14) 50–100 | (15) 20 | — |
| 21-Hydroxy (E & F) | (3) 10 | (4) 1.5 | — | — | — |
| Oxozoles (G & H) | (10) 6 | (11) 1 | (12) 120 | (13) 11 | — |
| (R)-4-Desmethyl (X₁) | (5) 20 | — | (16) 200 | (17) 20 | (28) 400 |
| (S)-4-Desmethyl (X₂) | (6) 7 | — | (10) 25–30 | (19) 12 | (29) 80 |
| 6-Desmethyl (X₃) | — | — | (20 1500 | — | — |
| 8-Desmethyl (X₄) | — | — | (21) 800 | — | — |
| 8,9-Dehydro (X₅) | — | — | (22) 1500 | (23) 200 | — |
| 10,11-Dehydro (X₆) | — | — | (24) 120 | — | — |
| 14-Hydroxy (X₇) | — | — | (25) | — | — |
| 16-Desmethyl (X₈) | (7) 20 | — | (26) 250 | — | — |
| 27-Hydroxy (X₉) | (8) 100 | — | (27) 200 | — | — |
| 21-Methyl (X₁₀) | — | (9) 1.5 | — | — | — |
| Compound | — | — | (36) 180 | — | — |
| Compound | — | — | (37) 50 | — | — |
| Compound | — | — | (38) 2000 | (39) 500 | — |

What we claimed is:

1. An epothilone of the formula:

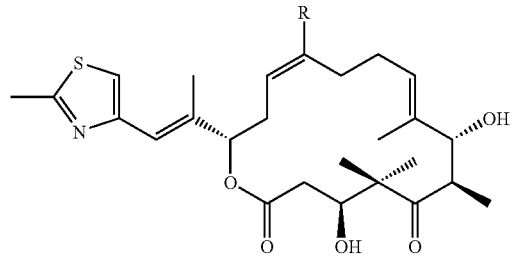

wherein:
for Epothilone C₅ (22) R═H or
Epothilone D₅ (23) R=methyl;
said epothilone having a state of purity such as to be substantially free of Epothilone A and Epothilone B.

2. The epothilone according to claim 1, wherein said epothilone is substantially free of other major metabolic products produced by DSM6773.

3. An epothilone of the formula:

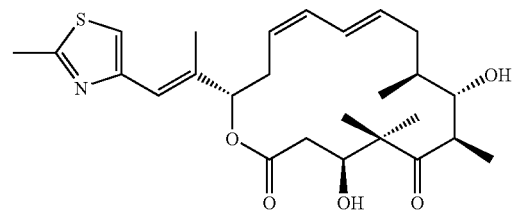

Epothilone C₆ (24);
said epothilone having a state of purity such as to be substantially free of Epothilone A and Epothilone B.

4. The epothilone according to claim 3, wherein said epothilone is substantially free of other major metabolic products produced by DSM6773.

5. An epothilone of the formula:

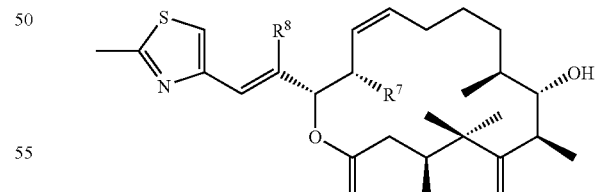

wherein:
for Epothilone C₇ (25) R⁷═OH; R⁸═methyl
or
Epothilone C₉ (27) R═CH₂OH; R⁷═H;
said epothilone having a state of purity such as to be substantially free of Epothilone A and Epothilone B.

6. The epothilone according to claim 5, wherein said epothilone is substantially free of other major metabolic products produced by DSM6773.

7. The epothilone according to claim 1, wherein said epothilone is substantially free of Epothilone D.

8. The epothilone according to claim 3, wherein said epothilone is substantially free of Epothilone D.

9. The epothilone according to claim 5, wherein said epothilone is substantially free of Epothilone D.

10. The epothilone according to claim 1, wherein said epothilone is substantially free of Epothilone C.

11. The epothilone according to claim 3, wherein said epothilone is substantially free of Epothilone C.

12. The epothilone according to claim 5, wherein said epothilone is substantially free of Epothilone C.

* * * * *

UNITED STATES PATENT AND TRADEMARK OFFICE
CERTIFICATE OF CORRECTION

PATENT NO. : 7,235,669 B2  
APPLICATION NO. : 11/354769  
DATED : June 26, 2007  
INVENTOR(S) : Gerhard Hoefle et al.

Page 1 of 1

It is certified that error appears in the above-identified patent and that said Letters Patent is hereby corrected as shown below:

In the Claims:

Claim 1:

Column 15, line 60, change "R=H" to -- R=H --.

Claim 5:

Column 16, line 62, change "$R^7$=OH" to -- $R^7$=OH --.

Column 16, line 64, change "R=CH$_2$OH; $R^7$=OH;" to -- $R^8$=CH$_2$OH; $R^7$=OH; --.

Signed and Sealed this
Sixteenth Day of October, 2012

David J. Kappos
*Director of the United States Patent and Trademark Office*